(12) United States Patent
Bristol et al.

(10) Patent No.: US 7,072,725 B2
(45) Date of Patent: Jul. 4, 2006

(54) IMPLANTABLE THERAPEUTIC SUBSTANCE INFUSION DEVICE CONFIGURATION SYSTEM

(75) Inventors: Guy Scott Bristol, Shoreview, MN (US); Peter Joseph Kovach, Fridley, MN (US); Keith Jasperson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 699 days.

(21) Appl. No.: 10/007,772

(22) Filed: Nov. 8, 2001

(65) Prior Publication Data

US 2002/0143580 A1 Oct. 3, 2002

Related U.S. Application Data

(60) Provisional application No. 60/278,820, filed on Mar. 26, 2001.

(51) Int. Cl.
*G06F 19/00* (2006.01)

(52) U.S. Cl. ............................. 700/90; 700/9; 700/281; 705/2; 604/65; 604/890.1; 702/188

(58) Field of Classification Search ..................... 700/9, 700/90, 281, 283; 702/188; 600/300; 604/65; 705/2

See application file for complete search history.

(56) References Cited

U.S. PATENT DOCUMENTS

| 4,766,542 | A |   | 8/1988 | Pilarczyk ..................... 364/413 |
| 5,389,078 | A |   | 2/1995 | Zalesky et al. ............. 604/151 |
| 5,781,442 | A | * | 7/1998 | Engleson et al. ........... 700/214 |
| 5,950,630 | A |   | 9/1999 | Portwood et al. ........... 128/897 |
| 5,970,466 | A |   | 10/1999 | Detjen et al. .................. 705/8 |
| 6,003,006 | A |   | 12/1999 | Colella et al. ................. 705/2 |
| 6,112,116 | A | * | 8/2000 | Fischell et al. ............. 600/517 |
| 6,167,309 | A |   | 12/2000 | Lyden |
| 6,234,973 | B1 |   | 5/2001 | Meador et al. ............. 600/486 |
| 6,249,705 | B1 | * | 6/2001 | Snell ........................... 607/59 |
| 6,558,320 | B1 |   | 5/2003 | Causey, III et al. ........ 600/300 |
| 2001/0037083 | A1 | * | 11/2001 | Hartlaub et al. ............. 604/65 |
| 2002/0128871 | A1 | * | 9/2002 | Adamson et al. .............. 705/3 |

FOREIGN PATENT DOCUMENTS

| WO | WO 84/01719 | 5/1984 |
| WO | WO 94/24929 | 11/1994 |
| WO | WO 96/13790 | 5/1996 |
| WO | WO 99/10029 | 3/1999 |
| WO | WO 99/44167 | 9/1999 |
| WO | WO 00/47108 | 8/2000 |

OTHER PUBLICATIONS

Medtronic brochure, "SynchroMed Infusion System", (1995).

* cited by examiner

*Primary Examiner*—Jayprakash N. Gandhi
(74) *Attorney, Agent, or Firm*—Fredrikson & Byron, P.A.

(57) ABSTRACT

The present invention provides for a software-based computing environment that uses data communication systems or networks, including the Internet and World Wide Web technologies, to implement a dosage calculator, which assists the clinician in managing patients receiving intrathecal therapy. The invention provides for a communications environment for clinicians, pharmacists, drug pump manufactures, and patients to assess the information supplied by an implantable drug pump, and to integrate data from other data sources in order to provide optimization of the life of the drug pump and the therapeutic substance formulations for the patient.

31 Claims, 31 Drawing Sheets

Fig. 6

PRIORITY
HEALTHCARE CORPORATION

Confirm Patient Prescription Reminder

Reminder has been scheduled. Click Submit to continue or Calendar to change.

| Patient Name | Last Rx | Next Rx | Change |
|---|---|---|---|
| John Doe | 28-Dec-2000 | 30-Jan-2001 | Calendar |

Submit

Rx REMINDERS — 56
PLACE NEW Rx — 46
TRACK Rx STATUS — 48
PATIENT HISTORY — 49

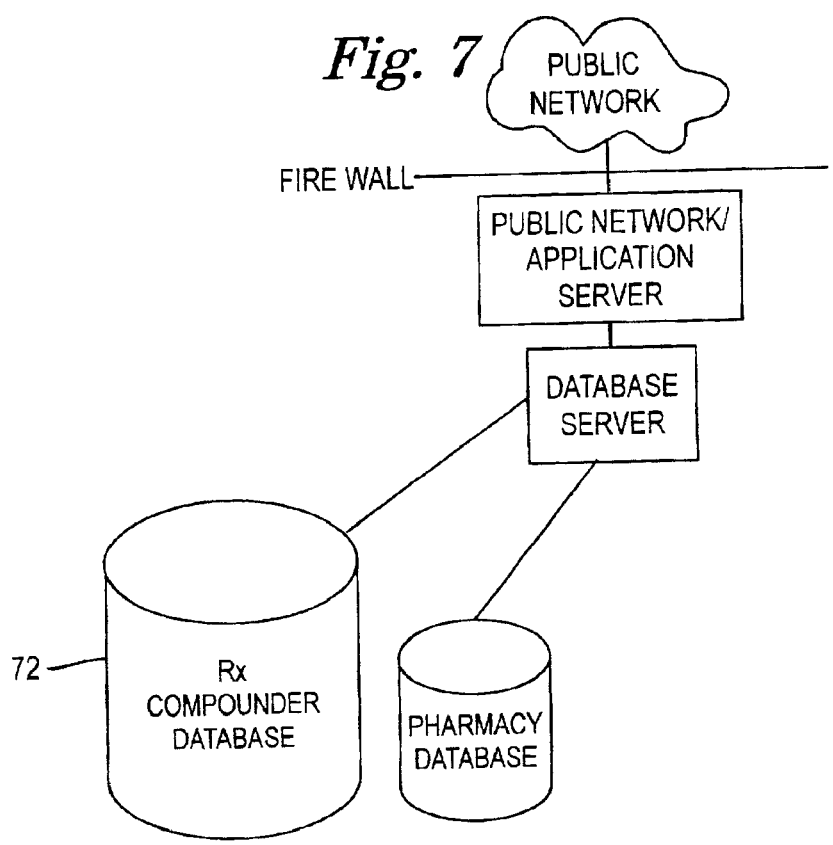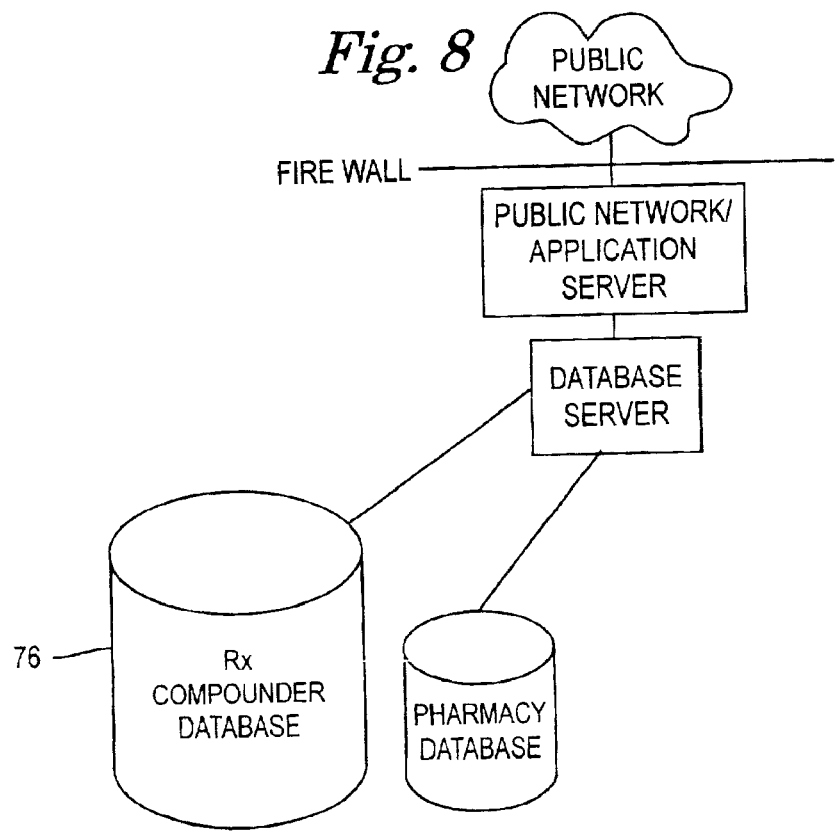

Fig. 9

PRIORITY HEALTHCARE CORPORATION

Order New Prescription

Select Patient: [_____] [SEARCH] (Last-name, First-name) — 96

Add New Patient+Prescription — 94

| Patient Name | ID | Actions | | |
|---|---|---|---|---|
| Jane Doe | 0823 | Rx History | Patient Profile | Rx |
| John Doe | 0488 | Rx History | Patient Profile | Rx |
| Michael Patient | 0787 | Rx History | Patient Profile | Rx |
| Jack Smith | 0123 | Rx History | Patient Profile | Rx |
| Mary Smyth | 0333 | Rx History | Patient Profile | Rx |

— 41, 43

[PLACE NEW Rx] — 46  [TRACK Rx STATUS] — 48  [PATIENT HISTORY] — 49

[Rx REMINDERS] — 56

Fig. 13

PRIORITY HEALTHCARE CORPORATION

Prescription-Referral Information

Patient Select is John Q. Doe (DOB. 1-Jan-1956, SSN 123-45-6789)

| Medication | Concentration (mg or mcg/ml) | Daily Dose (mg or mcg/day) |
|---|---|---|
| 1. Infumorph | 25 mg/ml | 1.5 ul/day |
| 2. | | |
| 3. | | |
| 4. | | |

Syringe volume (typically 10 or 20 ml): 20 ml — 1304

Fixed delivery rate or current programmed rate: 20 ml/day — 1306

Switch to Manual Rx — 1302

GO BACK — 1001   CANCEL — 1003   CONTINUE — 1005

Fig. 18

PRIORITY
HEALTHCARE CORPORATION

Patient History, Charts, Reports

Select Patient: [_1802_] [SEARCH] (Last-name, First-name)

| Patient Name | ID | Pharmacy | | | Medtronic | | |
|---|---|---|---|---|---|---|---|
| Jane Doe | 0823 | History | Chart | Print Report | ☐ | Pump Info. | |
| John Doe | 0488 | History | Chart | Print Report | ☐ | Pump Info. | |
| Michael Patient | 0787 | History | Chart | Print Report | ☐ | Pump Info. | 1808 |
| Jack Smith | 0123 | History | Chart | Print Report | ☐ | Pump Info. | |
| Mary Smyth | 0333 | History | Chart | Print Report | ☐ | Pump Info. | |

[PLACE NEW Rx] — 46
[TRACK Rx STATUS] — 48, 1806
[PATIENT HISTORY] — 49, 1804
[Rx REMINDERS] — 56

*Fig. 22*

PRIORITY
HEALTHCARE CORPORATION

Patient Registration (Part 1 of 4)
*Create new patient profile*

| Patient Name: | | ID: New |
| --- | --- | --- |
| Street Address: | (*** back-filled from DRS when available) | |
| City: | (***) | |
| Street Address: | (***) | |
| State: | Zip Code: | |
| Daytime Phone: | AAA-PPP-NNNN | Evening Phone: AAA-PPP-NNNN |
| * Date of Birth: | DD-MMM-YYYY | * Social Security No: NNN-NN-NNNN |

GO BACK — 1001
CANCEL — 1003
CONTINUE — 1005

Fig. 24

PRIORITY
HEALTHCARE CORPORATION

Patient Registration (Part 2 of 4)
*Patient emergency contact and medical information*

| Patient Name: New A. Patient | | ID:523 |

Emergency Contact: [ ]

Relationship: [ ]  Phone: [ ]

Allergies: [ ]

Height: [ ] cm   Weight: [ ]

Primary Diagnosis: [ ]  (pre-filled from DRS when available)

ICD9 Code: [ ]   Notes: [ ]

[GO BACK] — 1001    [CANCEL] — 1003    [CONTINUE] — 1005

*Fig. 25*

PRIORITY
HEALTHCARE CORPORATION

Patient Registration (Part 3 of 4)
*Patient Insurance Information.*

● Primary  ○ Secondary  ○ Tertiary

ID:523

Patient Name: New A. Patient

Insured Name:

Relationship:          DOB:

Insured SSN:

Insurance Company:

Insurance Phone:       Policy No:

Group Number:   Notes:

GO BACK — 1001    CANCEL — 1003    CONTINUE — 1005

*Fig. 26*

PRIORITY
HEALTHCARE CORPORATION

Patient Registration (Part 4 of 4)
*Patient Medical devices - Drug Pump*

| Patient Name: New A. Patient | | ID: 523 |
|---|---|---|

Infusion Pump: ○ Yes  ○ No   Manufacturer: [(***)]

Brand: [         ]   Model No: [(***)]

Implant Date: [(***)]   Reservoir Volume: [(parsed)] ml

Notes: [                    ]

[GO BACK] — 1001   [CANCEL] — 1003   [CONTINUE] — 1005

*Fig. 29*

NETSCAPE

FILE  EDIT  VIEW  GO  COMMUNICATION  HELP

Multiple Drug Calculation System

THE INFORMATION CAN BE CALCULATED USING THREE METHODS.

METHOD 1: ENTER THE DESIRED REFILL INTERVAL, FILL VOLUME, DRUG CONCENTRATION UNITS AND DAILY DOSE(S). THEN SELECT [CALCULATE CONCENTRATION].

METHOD 2: ENTER THE DESIRED REFILL INTERVAL, FILL VOLUME, DRUG CONCENTRATION UNITS AND CONCENTRATION(S). THEN SELECT [CALCULATE DAILY DOSE].

METHOD 3: ENTER THE DESIRED FILL VOLUME. THEN FOR THE DRUG 1 SELECT THE DRUG CONCENTRATION UNITS, CONCENTRATION AND DAILY DOSE. NEXT, SELECT [CALCULATE REFILL INTERVAL].

| REFILL INTERVAL IN DAYS (1-180) | | FILL VOLUME IN ML (0.1-18.0) | |
|---|---|---|---|
| DRUG NAME | CONCENTRATION (0-1000.0) | | DAILY DOSE (0-1000.0) |
| DRUG 1 | | ul ▸ /ml | ul |
| DRUG 2 | | ul ▸ /ml | ul |
| DRUG 3 | | ul ▸ /ml | ul |
| DRUG 4 | | ul ▸ /ml | ul |

[CALCULATE CONCENTRATION(S)]  [CALCULATE DAILY DOSE(S)]  [CALCULATE REFILL INTERVAL]

IMPLANTABLE THERAPEUTIC SUBSTANCE INFUSION DEVICE CONFIGURATION SYSTEM

CROSS-REFERENCE TO RELATED APPLICATIONS

This application claims the benefit of U.S. Provisional Application No. 60/278,820, filed Mar. 26, 2001, which is incorporated herein by reference in its entirety.

FIELD OF THE INVENTION

The present invention generally relates to an implantable therapeutic substance infusion device, also known as an implantable "drug pump." Specifically, the invention is an implantable drug pump configurer that considers aspects of the implantable pump along with specific drug formulations. More specifically the invention relates to real-time communication between physicians and the implantable therapeutic substance infusion device to assist the clinician in managing patients receiving therapy.

BACKGROUND OF THE INVENTION

Optimally, a technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide medical services in a manner independent of time and location.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is an implantable therapeutic substance infusion device.

An implantable therapeutic substance infusion device is implanted by a clinician into a patient at a location appropriate for the therapy. Typically, a therapeutic substance infusion catheter is connected to the device outlet and implanted to infuse the therapeutic substance such as a drug or infusate at a programmed infusion rate and predetermined location to treat a condition such as pain, spasticity, cancer, and other medical conditions. Many therapeutic substance infusion devices are configured in such a way that the device can be replenished with therapeutic substance through a septum while the device is implanted, so the time the device can be implanted may not be limited by therapeutic substance capacity. An example of an implantable therapeutic substance infusion is shown in Medtronic, Inc. product brochure entitled "SynchroMed® Infusion System" (1995). The infusion device has a housing; a power source; a therapeutic substance reservoir configured for containing a therapeutic substance and being refilled with the therapeutic substance while implanted; a therapeutic substance pump fluidly coupled to the therapeutic substance reservoir, and electrically coupled to the power source; and, electronics electrically coupled to the power source and coupled to the therapeutic substance pump. The electronics include a processor; memory coupled to the processor; an infusion program residing in memory, the infusion program capable of being modified once the therapeutic substance infusion device is implanted; and, transceiver circuitry coupled to the processor for externally receiving and transmitting therapeutic substance infusion device information.

An implantable therapeutic substance delivery device, also known as a drug pump, can be used for a wide variety of therapies such as pain, spasticity, cancer, and many other medical conditions. A clinician, such as a surgeon, in a sterile surgical procedure performed under local, regional, or general anesthesia typically implants the implantable therapeutic substance delivery device. The implantable therapeutic substance delivery device is generally implanted subcutaneously about 2.5 cm (1.0 inch) beneath the skin where there is sufficient subcutaneous tissue to support the implanted system. Once the therapeutic substance delivery device is implanted into the patient, the incision can be sutured closed and the therapeutic substance delivery device can begin operation.

The therapeutic substance delivery device operates to infuse a therapeutic substance at a programmed rate into a patient. The therapeutic substance is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance can be replenished in some embodiments of the implanted therapeutic substance delivery device by inserting a non-coring needle connected to a syringe filled with therapeutic substance through the patient's skin into a septum on the therapeutic substance delivery device to fill the implanted device reservoir. If the therapeutic substance delivery device requires replacement due to conditions such as battery depletion or other condition, an incision is made near the implanted therapeutic substance delivery device, and the old therapeutic substance delivery device is removed, also known as explanted. After the old therapeutic substance delivery device has been explanted, typically a new therapeutic substance delivery device is then implanted.

Prior art methods of clinical intrathecal therapy are generally limited to the implantable therapeutic substance infusion device's physical requirements. For example, if a physician needs to review the performance parameters of an implantable therapeutic substance infusion device in a patient, it is likely that the patient will have to go to the clinic. Further, if the medical conditions of a patient with an implantable therapeutic substance infusion device warrant a continuous monitoring or adjustment of the device, the patient would have to stay in a hospital indefinitely. Such a continued treatment plan poses both economic and social problems.

Currently, there is very little direct connectivity between the patient, the implantable drug pump manufacturer, the physician, the pharmacist, and the implantable device surgeon with the implantable drug pump. For instance, when the clinician implants a drug pump into a patient, the patient really has no other involvement with the implanted drug pump. Typically the patient merely conveys to the clinician their responses to their therapy during periodic medical appointments. Likewise, the clinician, implantable drug pump manufacturer, and pharmacist have no coordination with each other.

Presently, the clinician will receive the medical device and a manual of operation and installation containing generalized listings to assist the clinician in planning how to use the drug pump with a drug therapy. The listings are based upon an average of drug pump parameters and likely real-life scenarios which are made quite conservative to avoid the risk of failure of the drug pump while installed inside the patient. Therefore, the only way for a clinician to get a better understanding of the technical characteristics of the drug pump is reading the drug pump manual or a possible discussion with a drug pump technical representative.

The pharmacist's coordination with other drug pump stakeholders is limited as well. The pharmacist typically will receive a drug pump medication prescription by fax, mail, or delivery; then fill the prescription and deliver the medication to the clinician. Therefore, no interaction occurs between the pharmacist, clinician, drug pump manufacturer, and patient. This is a very compartmentalized way of performing intrathecal therapy with minimal information interchanged. Thus the capabilities of the implantable drug pump and the capabilities of the therapeutic substances are not optimized.

Electrically powered implanted therapeutic substance infusion devices can require replacement once implanted due to factors such as battery consumption, corrosive damage, and mechanical wear. Since replacement of the implanted device requires an invasive procedure of explanting the existing device and implanting a new device, it is desirable to only replace the infusion device when replacement is required. Replacement of previous implantable infusion devices was typically scheduled based upon a worst-case statically forecasted elective replacement period. The worst-case scenario typically resulting in the implanted infusion device being replaced several months or even years before the implanted infusion device required replacement. Some previous implantable pulse generators such as pacemakers have monitored a single sensed battery condition to estimate replacement time for the implanted device or battery such as shown in U.S. Pat. No. 6,167,309 "Method For Monitoring End Of Life For Battery" by Lyden (Dec. 26, 2000).

For the foregoing reasons, it would be desirable, in connection with the implantation of therapeutic substance infusion devices to provide a system by which the lifespan of the device could be predicted, thus increasing the infusion device's effective life, reducing the need for a clinician to perform static longevity forecasts for therapy changes, facilitate a broader range of possible elective replacement scheduling for the convenience of the patient and clinician, and many other improvements.

Dosage calculators in some form are currently available for clinicians to use. However, because present dosage calculation systems do not provide the patients, other clinicians, pharmacists and dispensaries, and drug pump manufactures with connectivity to each other. These devices operate with a minimum of real-world information from these valuable sources of pertinent information. Further, prior art dosage calculators don't provide the ability to view patient's drug history, e.g. and intrathecal drug history, and assess drug dosage trends or perform a convenient detailed check of a patient's information such as drug allergies. Finally, the prior art devices do not take into account the detailed specification of the implanted drug pump when therapeutic substance infusion therapy, such as intrathecal therapy, is being prepared. Currently the clinician may have some very broad parameters of the pump. For example, the clinician might have the implantable pump's drug reservoir volume, or they might know the ranges in which the infusion rates operate. However, such general parameters yield a prediction of dosage and device lifespan, which could be improved upon.

The proliferation of patients with implantable drug pumps worldwide has made it desirable to provide remote services to the drug pumps and timely clinical care to the patient. Frequent use of programmer devices to communicate with implantable medical devices and provide various remote services, consistent with U.S. patents and co-pending applications: U.S. Pat. No. 6,250,309 titled "System and Method for Transferring Information Relating to an Implantable Medical Device to a Remote Location," filed on Jul. 21, 1999; U.S. Pat. No. 6,442,433 titled "Apparatus and Method for Remote Troubleshooting, Maintenance and Upgrade of Implantable Device Systems," filed on Oct. 26, 1999; U.S. Pat. No. 6,644,321 titled "Tactile Feedback for Indicating Validity of Communication Link with an Implantable Medical Device," filed Oct. 29, 1999; U.S. Pat No. 6,385,593 titled "Apparatus and Method for Automated Invoicing of Medical Device Systems," filed Oct. 29, 1999; "Apparatus and Method for Remote Self-Identification of Components in Medical Device Systems," filed Oct. 29, 1999, Ser. No. 09/429,956 a continuation of which has issued as U.S. Pat. No. 6,754,538; U.S. Pat. No. 6,363,282 titled "Apparatus and Method to Automate Remote Software Updates of Medical Device Systems," filed Oct. 29, 1999; "Method and Apparatus to Secure Data Transfer From Medical Device Systems," filed Nov. 2, 1999, Ser. No. 09/431,881; U.S. Pat. No. 6,411,851 titled "Implantable Medical Device Programming Apparatus Having An Auxiliary Component Storage Compartment," filed Nov. 4, 1999; U.S. Pat. No. 6,386,882 titled "Remote Delivery Of Software-Based Training For Implantable Medical Device Systems," filed Nov. 10, 1999; U.S. Pat. No. 6,418,346 titled "Apparatus and Method for Remote Therapy and Diagnosis in Medical Devices Via Interface Systems," filed Dec. 14, 1999; U.S. Pat. No. 6,497,655 titled "Virtual Remote Monitor, Alert, Diagnostics and Programming For Implantable Medical Device Systems" filed Dec. 17, 1999; "Implantable Therapeutic Substance Infusion Device with Active Longevity Projection" filed Mar. 16, 2001, Ser. No. 09/809,809; "Implantable Medical Device Management System," filed on Mar. 26, 2001, Ser. No. 06/278,821; which are all incorporated by reference herein in their entirety, has become an important aspect of patient care. Thus, in light of the disclosures herein, the present invention provides a vital system and method of dispensing/delivering efficient therapy and clinical care to the patient.

SUMMARY OF THE INVENTION

Therefore it is the object of the present invention to provide for real-time communication between clinicians and the implantable therapeutic substance infusion device to assist clinicians in managing patients receiving intrathecal therapy. For example, the present invention may be implemented over the Internet using a secure protocol. More specific objects of the invention are to provide for drug dosage calculations given refill interval, reservoir size, drug concentration units and concentration of drugs in the pump; to provide drug concentration calculations given the refill interval, reservoir size, concentration units and daily doses; to provide drug refill calculations given the drug concentration units, concentration of drugs in the pump, and daily doses; to enable physicians to calculate hypothetical dosage calculations utilizing the above listed variables; to reduce the opportunity for the pump to run dry; to minimize the potential for overdose; to accommodate deletions or additions to the intrathecal drug mixture; to provide the physician with the capability to recall patients drug records; to allow the physician to view patient intrathecal drug history and assess drug and dosage trends; and to provide Internet or Web links to stability references on selected drugs and concentrations.

The present invention provides for a software-based environment that uses data communication systems or networks, including the Internet and World Wide Web technologies, to implement a dosage calculator, which may be used to assist the clinician in administering treatment, e.g., intrathecal therapy, to patients being treated with a therapeutic agent. It is desirable to provide medical professionals with integrated data to manage patient care. Implantable drug pumps, for example, can supply robust data associated with and stored within the drug pump. The invention provides for a communications environment for clinicians, pharmacists, drug pump manufactures, and patients to assess not only the information supplied by an implantable drug pump, but also integrate data from other data sources, such as pharmacies, therapeutic agent producers, implantable device manufacturers, other treatment providers, and the like.

The present invention provides for an inexpensive and practical way for a physician to review the performance parameters of an implantable drug pump in a patient to provide optimization of the life of the drug pump and the therapeutic substance formulations for the patient.

BRIEF DESCRIPTION OF THE DRAWINGS

FIG. 6 is a representation of an interface display for a Confirm Patient Prescription-Reminder function according to one implementation of the present invention.

FIG. 7 is a network architecture diagram of a database server.

FIG. 8 is a network architecture diagram of a database server.

FIG. 9 is a representation of an interface display for an Order Prescription function according to one implementation of the present invention.

FIG. 13 is a representation of an interface display for a "Manual Prescription Entry" function according to one implementation of the present invention.

FIG. 18 is a representation of an interface display for a "Patient History" function according to one implementation of the present invention.

FIG. 22 is a representation of an interface display for a "Patient Registration" function according to one implementation of the present invention.

FIG. 24 is a representation of an interface display for a "Patient Registration Emergency Contract" function according to one implementation of the present invention.

FIG. 25 is a representation of an interface display for a "Patient Insurance Registration" function according to one implementation of the present invention.

FIG. 26 is a representation of an interface display for a "Medical Devices Registration" function according to one implementation of the present invention.

FIG. 29 is a representation of an interface display for a "Multiple Drug Calculation" function according to one implementation of the present invention.

DETAILED DESCRIPTION OF PREFERRED EMBODIMENT

To assist in an understanding of the invention, a preferred embodiment or embodiments will now be described in detail. Reference will be made to the drawings, which are summarized above.

Figure 1:
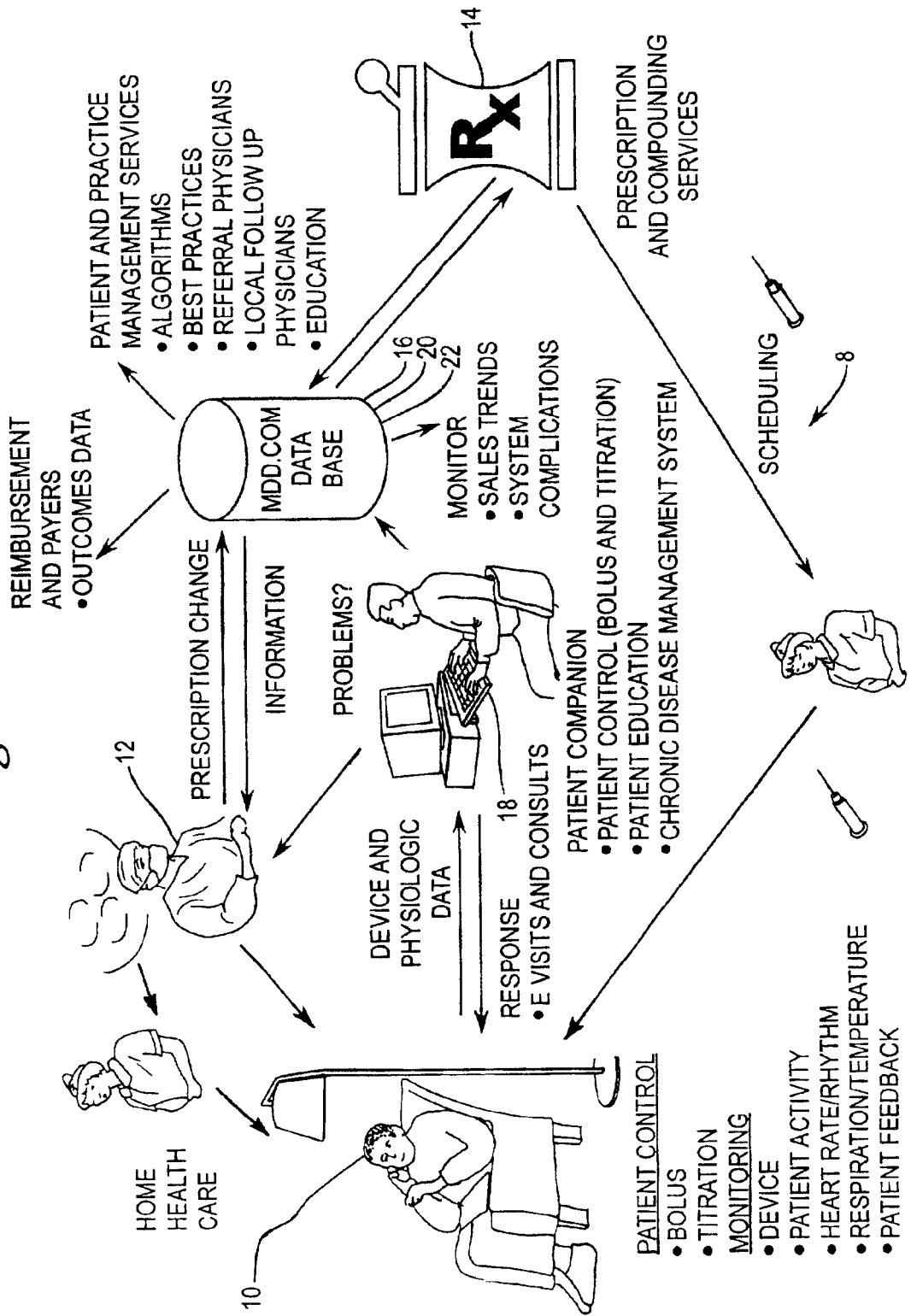
FIG. 1 is a diagrammatic representation of the interaction between various end users in an implantable drug pump configuration system according to the present invention.

FIG. 1 is a diagrammatic representation of a connectivity system according to the present invention. The diagrammatic representation of connectivity system 8 shows the interaction between the pharmacist 14, clinician 12, drug pump manufacturer 18, and patient 10. Patient 10, clinician 12, prescription provider 14, drug database 16, and drug pump manufacturer 18 all have connectivity to one another over a data communications network, which may include a public internetwork such as the Internet. In the present invention, patient 10 may be provided the capability to exercise some control over their own therapy as warranted or as permitted by clinician 12, as well as providing, via an implanted drug pump or other implanted medical device, detailed physiological data pertaining to patient 10 such as heart monitoring, respiration monitoring, or temperature monitoring. Drug pump information and the patient's physiological data are communicated to a central location 20, which for the purposes of the preferred embodiment may be the device manufacturer or central server administered by the device manufacturer, depicted as server 20. Once the central server 20 has the drug pump and patient 10 physiological data the data is then inputted into a database 22, depicted as a drug pump manufacturer database "MDD.com Data Base" 22.

When clinician 12 registers the implantable drug pump's serial number via connectivity system 8 (discussed infra), he or she may be provided with extensive information regarding the implanted pump. Clinician 12 is able to discover such information as whether a specific catheter is compatible with certain therapeutic substances, therapies or stress forces that the pump places on the therapeutic substance during pumping at different pumping rates. For example, certain stresses on therapeutic substances, such as pressure, alter the therapeutic substance through the actual pumping activity, such as a biologic or genetic material, which have constraints on the types of stresses the material may be exposed to before affecting the therapeutic properties of the agent. Therefore, having all of the implantable drug pump information assists clinician 12 in developing the intrathecal or other substance-release therapy and selecting an appropriate therapeutic agent.

Since clinician 12 can obtain extensive information in regard to the implantable drug pump, care of patient 10 may be improved. By optimizing the capabilities of the implantable drug pump and the capabilities of the therapeutic substances, patient 10 may be expected to benefit. For example, by optimizing the capabilities of the implantable drug pump and the capabilities of the therapeutic substances, as well as more accurately predicting the expected life of the drug pump, without providing for an overly conservative regimen or projected life for the device, or the treatment life of the drug pump, can more accurately be determined and therefore the patient 10 would not need their pump explanted until a later time. This benefits patient 10 and the insurance company that may be paying for the explanting procedure.

Another advantage to connectivity system 8 is that the drug pump manufacturer can receive instantaneous positive and negative feedback from all of the stakeholders. For example, by examining the extensive information feedback from clinicians, the drug pump manufacturer can discover that the pump is operating longer than they had expected it to and thus allow for the extension of the pump's expected life. Another example is where the drug pump manufacturer examines the extensive feedback information and discovers that in particular pumps a certain component, e.g. a gear, is failing at a time earlier than expected. If the drug pump manufacturer learns of such trend data they can instantaneously target the specific clinicians 12 and patients 10 that really ought to be concerned about that particular pump.

With reference to FIG. 1, a clinician 12 is able to directly communicate a prescription change to pharmacist 14 via connectivity system 8 database. Clinician 12 inputs the prescription change and when the database receives the prescription change pharmacist 14 is immediately notified of the prescription change.

FIGS. 2–32 show an implementation of connectivity system 8 specifically towards a drug calculator. Certain interface displays depict a generic "Priority Healthcare" entity, which may for purposes of this invention generically represent any interested healthcare provider or clinician 12.

The present invention may be combined with an active longevity projection system, such as that disclosed by the pending application, assigned in common to the assignee of the instant invention, "Implantable Therapeutic Substance Infusion Device with Active Longevity Projection" filed Mar. 16, 2001, Ser. No. 09/809,809, which is hereby incorporated in its entirety into the instant application. In combination with the active longevity projection system, the present invention may allow dynamic monitoring of the state of a medical device, allowing more accurate prediction of an elective replacement period for the infusion device to increase the infusion device's effective life, reduce the need for a clinician 12 to perform static longevity forecasts for therapy changes, and facilitate elective replacement scheduling for the convenience of the patient 10 and clinician 12, and many other improvements. The dynamically updated data may be used in conjunction with an active longevity projection program that correlates at least one preset parameter to at least one sensed parameter to calculate an updated or confirmed elective replacement period for the infusion device. The preset parameter may reside in device memory and is indicative of longevity of the infusion device. The sensed parameter is accessible by the processor indicative of longevity of the infusion device. Many embodiments of the therapeutic substance delivery device with active longevity projection and its methods of operation are possible.

One group of data that may be communicated between a patient-implanted device and the clinician 12, via a central server is sensed longevity parameters that may be stored on the implanted device. Such longevity parameters may be any measurable parameter that correlates to longevity of the therapeutic substance infusion device such as implant time, elapsed implant time, battery voltage, mechanical indication, and the like. The mechanical indication can be any parameter that either directly or indirectly measures a mechanical operation in the therapeutic substance infusion device such as therapeutic substance pump cycles, therapeutic substance pump torque, corrosion, and the like. When the desired mechanical indication is therapeutic substance pump cycles, one embodiment uses a motor drive monitor coupled to the electronics for counting the number of therapeutic substance pump cycles.

The longevity prediction program serves as a means for predicting longevity of the implantable therapeutic substance infusion device by correlating the preset parameter to the sensed parameter to calculate an elective replacement period for the implantable therapeutic substance infusion device. The longevity prediction program reports an elective replacement indicator in advance of an end-of-life period for the implantable therapeutic substance infusion device. The elective replacement indicator can be annunciated via the communications network provided according to the present invention. The elective replacement indicator permits the implantable therapeutic substance infusion device to be operated in practice closer to the end-of-life period for the implanted therapeutic substance infusion device by monitoring battery longevity, accumulated pump revolutions, and motor drive. A therapy program approved by the treating clinician 12 typically controls operation of the implantable therapeutic substance infusion device. A wide variety of therapy programs can be used in the therapeutic substance infusion device with each therapy program having operating parameters that can affect the elective replacement period and end-of-life for the therapeutic substance infusion device such as drug formulation, therapy, implant time, and the like.

The sensed parameter may be any measurable parameter indicative of longevity such as elapsed implant time, battery voltage, a mechanical parameter, and the like. The mechanical parameter can be therapeutic substance pump cycles, therapeutic substance pump torque, corrosion, and the like.

The longevity prediction program calculates an elective replacement period for the implantable therapeutic substance infusion device by correlating the preset parameter with the sensed parameter. In one embodiment, the longevity program may calculate elective replacement period that can be determined by corrosion, battery longevity, and mechanical longevity depending upon the manner the infusion pump operated.

The elective replacement period is reported as an elective replacement indicator to permit the clinician 12 or patient 10 to consider options before replacement of the therapeutic substance infusion device is required when the device reaches its end-of-life. The elective replacement indicator can be reported in any way that permits the clinician 12, patient 10, or both to be aware of the elective replacement period such as sending a SMTP protocol message (an "e-mail") to the clinician 12 and/or patient 10. Alternatively, the clinician 12 or patient 10 may access such information using a browser-based technology after the information is posted to a secure central server. The elective replacement indicator can permit the implantable therapeutic substance infusion device to be operated closer to an end-of-life period for the implanted therapeutic substance infusion device thereby extending an effective life of the implantable therapeutic substance infusion device.

Monitoring or posting to a central server may be increased after a certain "pre-end-of-life (EOL)" threshold has been met. Upon notification over communications network 8, clinician 12 may determine whether any throttle system functions should override the longevity extension program and cause the infusion device to continue operation as programmed. Thus the present invention permits a clinician 12, if so desired, to perform updated static longevity forecasts for therapy changes, facilitating elective replacement scheduling for the convenience of patient 10 and clinician 12.

Figure 2:
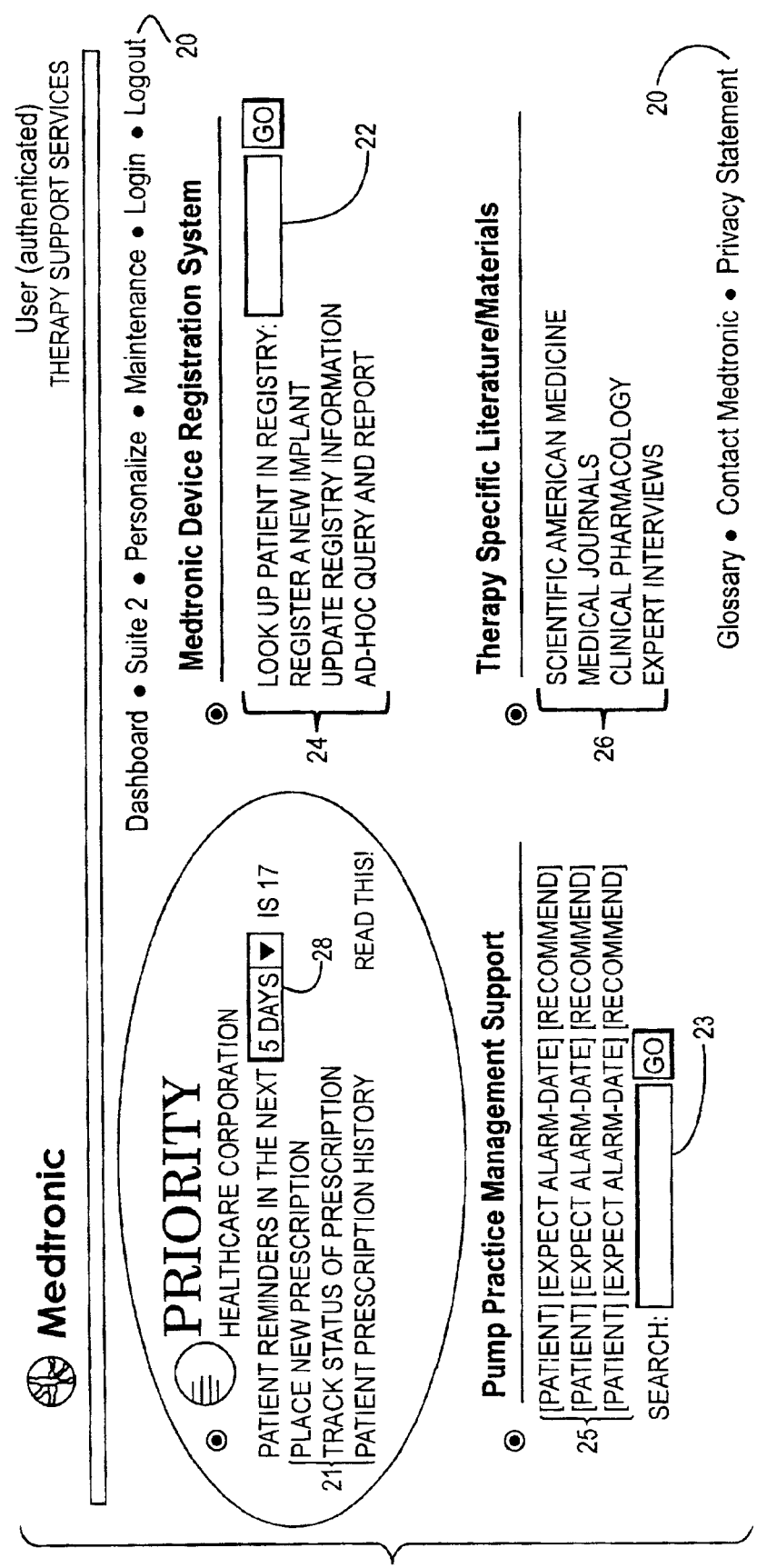
FIG. 2 is a representation of an interface display for a remote maintenance and/or configuration utility according to one implementation of the present invention.

With reference to FIG. 2, in a preferred embodiment, the present invention is implemented with a remote maintenance and/or configuration utility, for example, over a data communications network. The remote configuration capability of the system may be implemented as a computer program or application on a computer, for example, a personal computer. A physician who has a patient 10 with an implantable drug pump according to the present invention may execute the remote configuration computer program. The physician's computer may be programmed to receive authenticated user credentials from a centralized authentication server. This server may be accessed via any suitable data communications network. For example, the credentials may be accessed via TCP/IP. If the user accesses the credentials via a public network or internetwork such as the Internet, preferably an encrypted or secure protocol, e.g. secure socket layer security, will be implemented to protect the authentication data from misappropriation. The user may be presented with a GUI element, such as a browser-based interface.

FIG. 2 displays a "Portal" where pharmacist 14, clinician 12, drug pump manufacturer 18, and patient 10 may utilize the present invention. From the portal the user can perform basic application functions such as login or logout of the application, perform maintenance on their account, contact the application's administrator, or personalize the application from tool bar 20. Further, the user can perform application specific functions such as registering an implantable device, obtaining current medical and pharmacological reference materials, obtaining or tracking the status of a prescription, or performing pump practice management. With the device registration function the user can input a patient's name into box 22 to see if the patient 10 is in the registry. In addition, the user could also register a new implant, update the registry, or perform a search of the application by clicking on hyperlinks 24. With the therapy specific literature function the user can research various related topics concerning implantable devices through hyperlinks 26. A clinician 12 could determine the number of patients who are due for prescriptions within a user defined time period utilizing scroll box 28. Moreover, the clinician 12 could place a new prescription, track the status of a prescription, and find a patient's prescription history by clicking on hyperlinks 21. The clinician 12 could also obtain implantable pump technical support by entering a search term in box 23 or by clicking on hyperlinks 25 when a patient 10 recommendation is shown. In the preferred embodiment the user would be able to access most any functionality of the application through the application "Portal".

Figure 3:
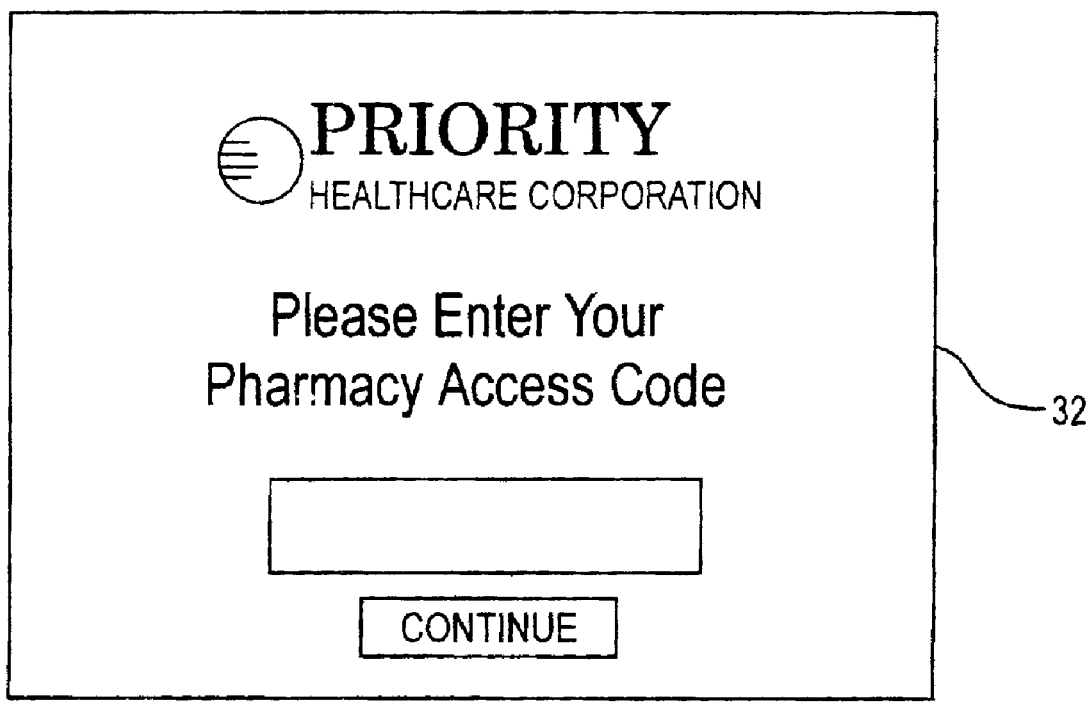
FIG. 3 is a representation of an interface display for initial access or execution of the application according to one implementation of the present invention.

With reference to FIG. 3, upon application startup by a remote user, for example, a clinician 12 seeking to ready a device for implantation, and following authentication of the user by a central server on which authentication application is stored, the application will receive authenticated user credentials from a central server on which these credentials are stored. In this way, a virtually "tunneled" access socket may be established for future communications between the remote application and the central server. The authentication may be based, e.g. on User_ID together with a "Proxy Authority" (list of Physician User IDs).

Upon initial access or execution of the application, the user may be presented with a user interface or display, such as pop-up box 32 prompting the user to enter a "Pharmacy Access Code", or other suitable authentication criteria or passphrase as just discussed above. Typically, this pop up box may appear when the user chooses to "place new prescription" from the portal shown in FIG. 2. Then the user inputs their User_ID together with a "Proxy Authority" into box 34 to gain access to the "place new prescription" function.

The communication between the clinician 12 user and a central pharmacy or medical device server may take place via, for example, an XML Document with the following or other suitable tags: prefix (title, e.g., Dr.), First, Middle, and Last Name, Suffix (e.g., M.D.), Role, Specialty. The physician or other clinician 12 may alternatively, or in addition, enter a Practice_Group_ID. In this way, a physician or clinician 12 may access patient 10 information for a group of patients that are treating with a certain clinical entity. These may be generally referred to as "associated patients". In either event, upon authentication of the user, the application may present a thumbnail, reduced, or summary view of a variety of data that may be useful or of interest to the clinician 12. These may include, for example, the number of pending prescriptions or prescription requests for associated patients. This data will provide a "tickler" or reminder function for a clinician 12 as to prescription matters which should be attended to. The summary or reduced size data may also include, for example, a list of pharmacy commands, e.g., patient 10 prescriptions due or pending, place new prescription, track a prescription status, or view a patient 10 prescription history. The interface may also display user warnings and disclaimers suitable for the medical professional or clinician 12.

Figure 4:
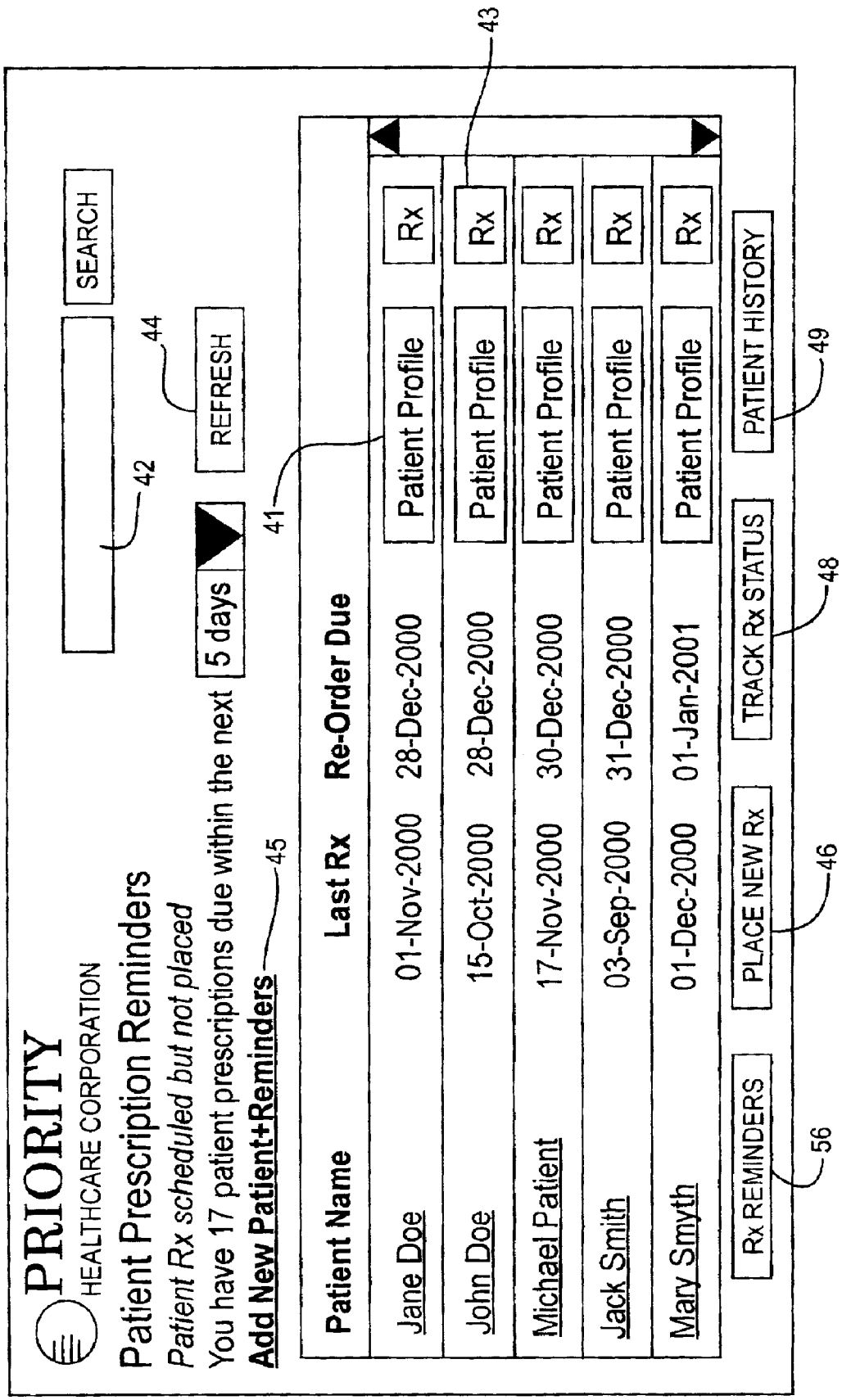
FIG. 4 is a representation of an interface display for a Patient Prescription-Reminder function according to one implementation of the present invention.

With reference to FIG. 4, in a preferred embodiment of the present invention, the data communications portal or interface provides for a Patient Prescription-Reminder function to the end user, such as a clinician 12. The reminder function can allow the clinician 12 to view each of their patients in which a prescription is due within a user defined time period. Moreover, the clinician 12 can search for a specific patient 10 utilizing search box 42. Similar to the "Portal" the user is able to adjust patient 10 prescription reminder timeframe by utilizing scroll box 44. From the reminder function the user can choose several other functions such as placing a new prescription by clicking on box 46, tracking a prescription by clicking on box 48 and viewing patient 10 history by clicking on box 49. Further, the clinician 12 can click on box 41 and obtain the patient's full medical profile or click on box 43 and view all of the patient's prescription(s). Executing the "Rx" or similar GUI element "button" may also be used to initiate the Order Prescription process for the corresponding patient 10 listed.

Figure 5:
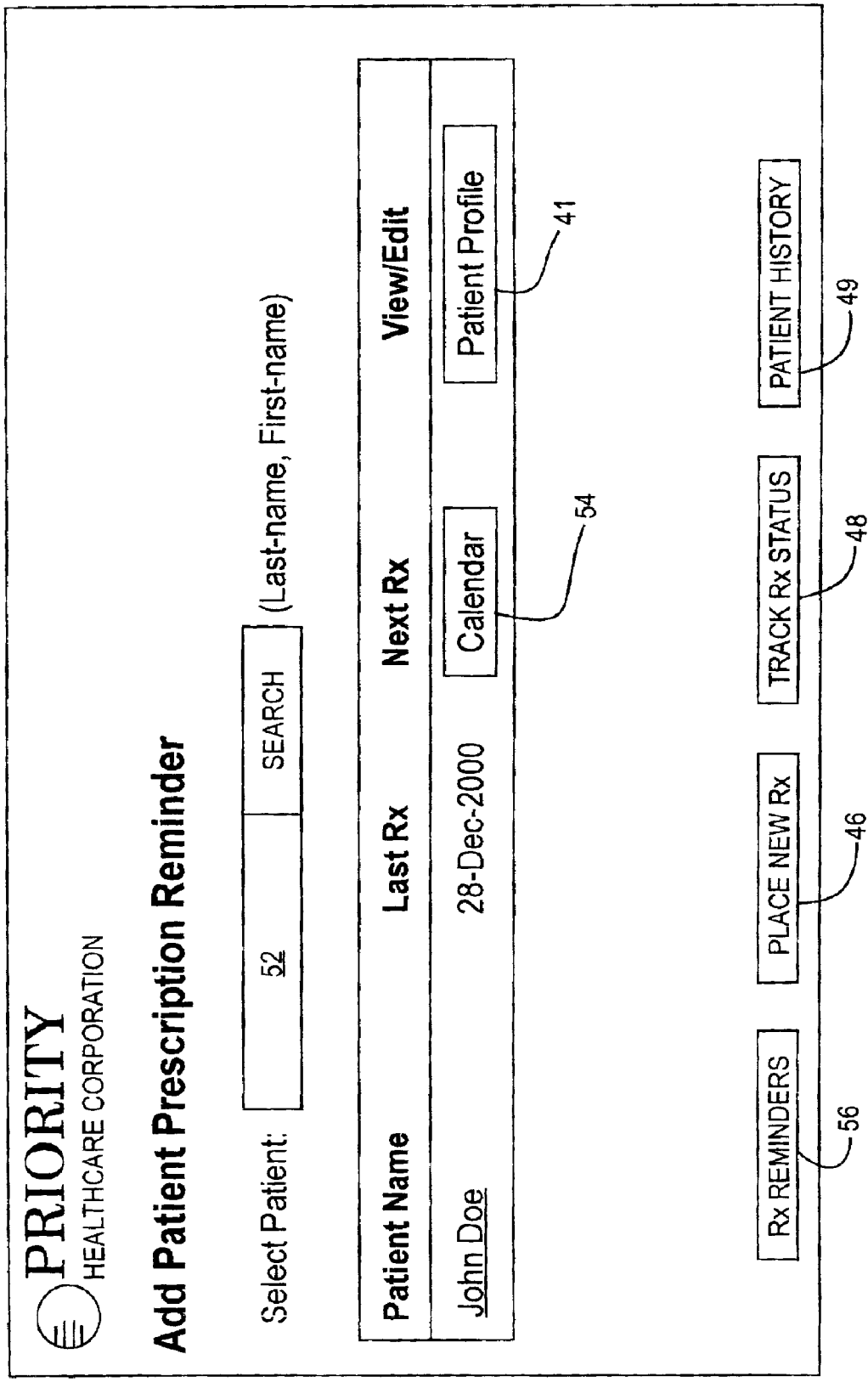
FIG. 5 is a representation of an interface display for an Add Patient Prescription-Reminder function according to one implementation of the present invention.

With reference to FIG. 5, the user may enter an instruction to the prescription reminder application to "Add a New Patient-Reminder". Or for example, when the "Add New Patient-Reminder" hyperlink 45 is executed from the "Patient Prescriptions Due" screen, or a "Select Patient" search command does not find the patient 10, the Patient Registration process may be initiated automatically by the interface program. The user can perform a search to insure that a patient 10 reminder does not already exist by inputting the patient's name into box 52 and clicking on the search GUI element element button. Calendar GUI element element button 54 allows the clinician 12 to schedule the patient's up coming prescription needs. Calendar button 54 may initiate an interactive pop up GUI element element box representation of a calendar or the like to allow the clinician 12 to make user-friendly prescription inputs. The user can also return to the Rx reminder screen by clicking on GUI element element button 56. In these cases, the Rx Reminder process will preferably immediately follow completion of new patient 10 registration. Further, with reference to FIG. 6, the user is prompted to confirm the patient 10 prescription reminder either by submitting the current patient 10 prescription data by clicking on GUI element element button 62 or changing the patient 10 prescription data by clicking on GUI element element button 54 to reflect the proper data.

With reference to FIG. 7, it will be preferable, in order to avoid duplicate patient 10 registration entries, that the "Add New Patient" function will check the existing database 72 for duplicate patient 10 entries, and prompt the user to indicate whether this is the same person, or a different patient 10 with a coincident same name.

With reference to FIG. 8, preferably, to avoid duplicate patient 10 registration entries, the "Add New Patient" function must check the existing database for duplicates and prompt the user if this is the same person or a different patient 10 with the same name. The "Select Patient" search and "Patient Registration" processes are detailed later.

Another clinician 12 task, which may be automated according to the present invention, may be termed the "Order Prescription" task. When the "Add New Patient" or like command is executed from the "Order New Rx" interface, or a "Select Patient" search command does not find the patient 10, the patient 10 registration process will begin. In these cases the "Order Prescription" process will immediately follow completion of new patient 10 registration. Executing the "Rx" button will begin the "Order Prescription" process for the corresponding patient 10 listed.

With reference to FIGS. 9, the "Order Prescription" process may be implemented as a network communication for pharmacies that are enabled to receive such network orders. From the order prescription function the user is able select a patient 10 from a clinicians patient list or add a new patient 10 and then enter a prescription for the patient 10. The clinician 12 can perform a search for a patient 10 by inputting the name into box 92 and clicking on the search GUI element element button. The clinician 12 can add a new patient 10 and prescription by clicking on hyperlink 94. In addition, the user can view the patient's entire prescription history by clicking on GUI element element button 96.

Figure 10:
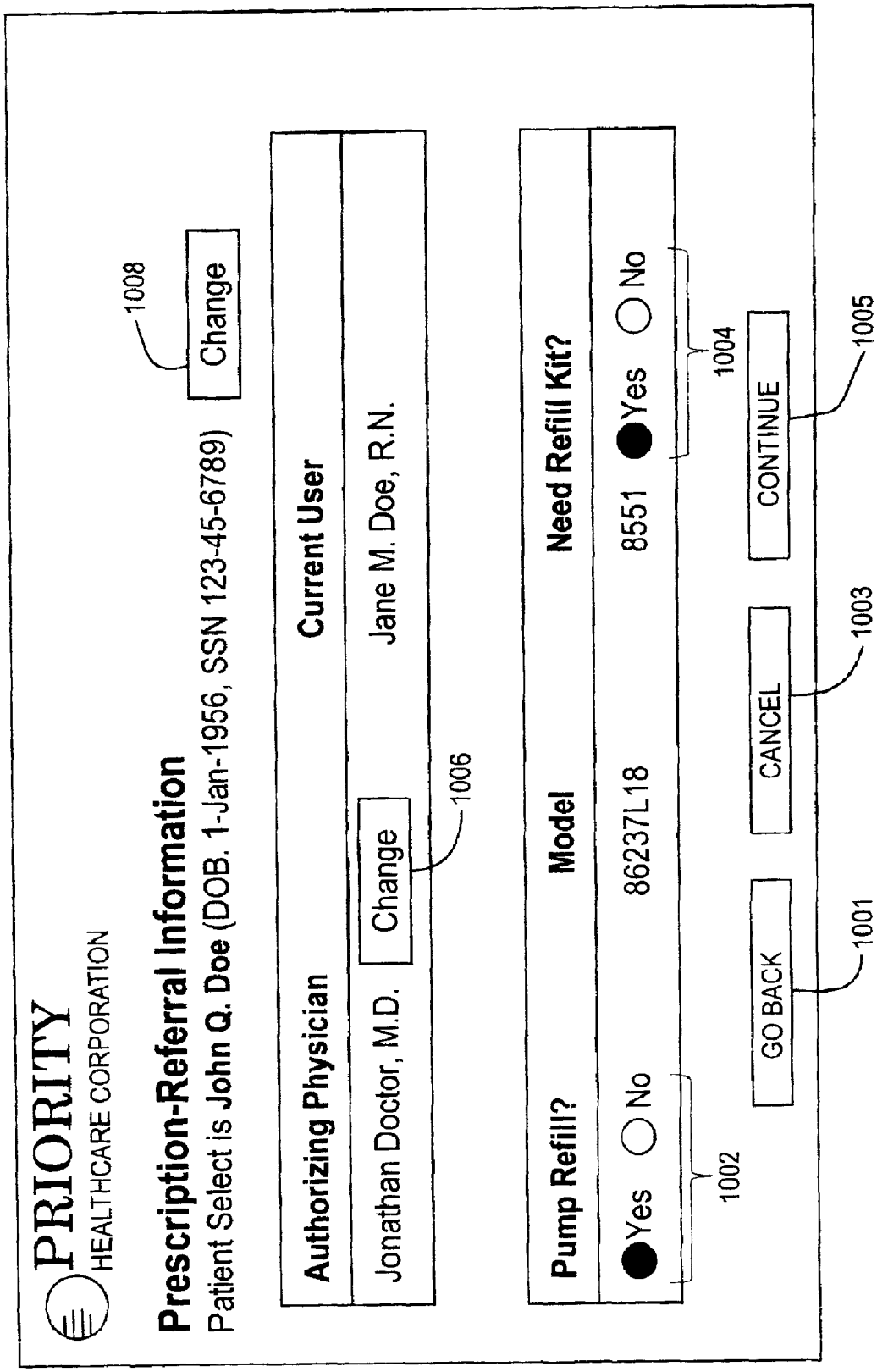
FIG. 10 is a representation of an interface display for a Select Proxy and Pump function according to one implementation of the present invention.

With reference to FIG. 10, when the application user chooses to order a prescription, the network allows a physician to perform a "Select Proxy and Pump" process where a clinician 12 is able to order a pump refill by clicking on status bulbs 1002, a refill kit by clicking on status bulbs 1004, or change the authorizing physician for the patient 10 by clicking on GUI element element button 1006. If the clinician 12 decides to change the authorizing physician, a pop-up window may appear with a listing of eligible physicians who can replace the current authorizing physician. If the clinician 12 discovers that the wrong prescription referral information is showing, the clinician 12 can click on GUI element element button 1008 to return to the "Order Prescription" function as shown in FIG. 9. When the proxy and pump process is complete the clinician 12 can decide to "Go Back" with GUI element button 1001, "Cancel" the process with GUI element button 1003, or "Continue" the process with GUI element button 1005. When "Continue" button 1005 is chosen, the user is taken to the "Order Prescription" function as shown in FIG. 11.

Figure 11:
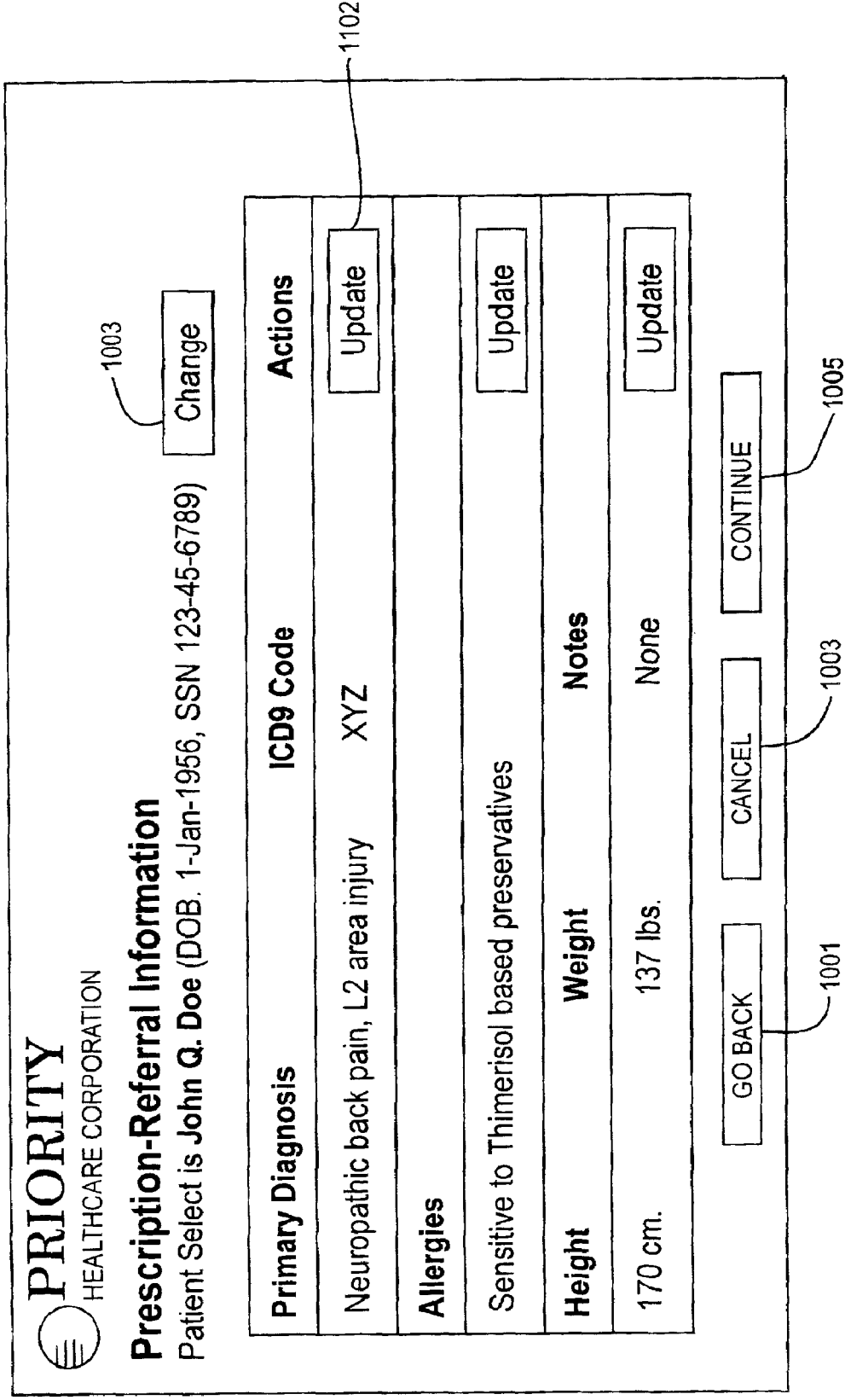
FIG. 11 is a representation of an interface display for another Order Prescription function according to one implementation of the present invention.

With reference to FIG. 11, inside of the "Order Prescription" process a clinician 12 is able to update a patient's referral information, such as the patient's primary diagnosis, any allergies, or any personal information. If any of this information is incorrect or incomplete, the user can click on the "Update" GUI element 1102 and make any necessary adjustments to the patient's referral information in a separate pop up window.

Figure 12:
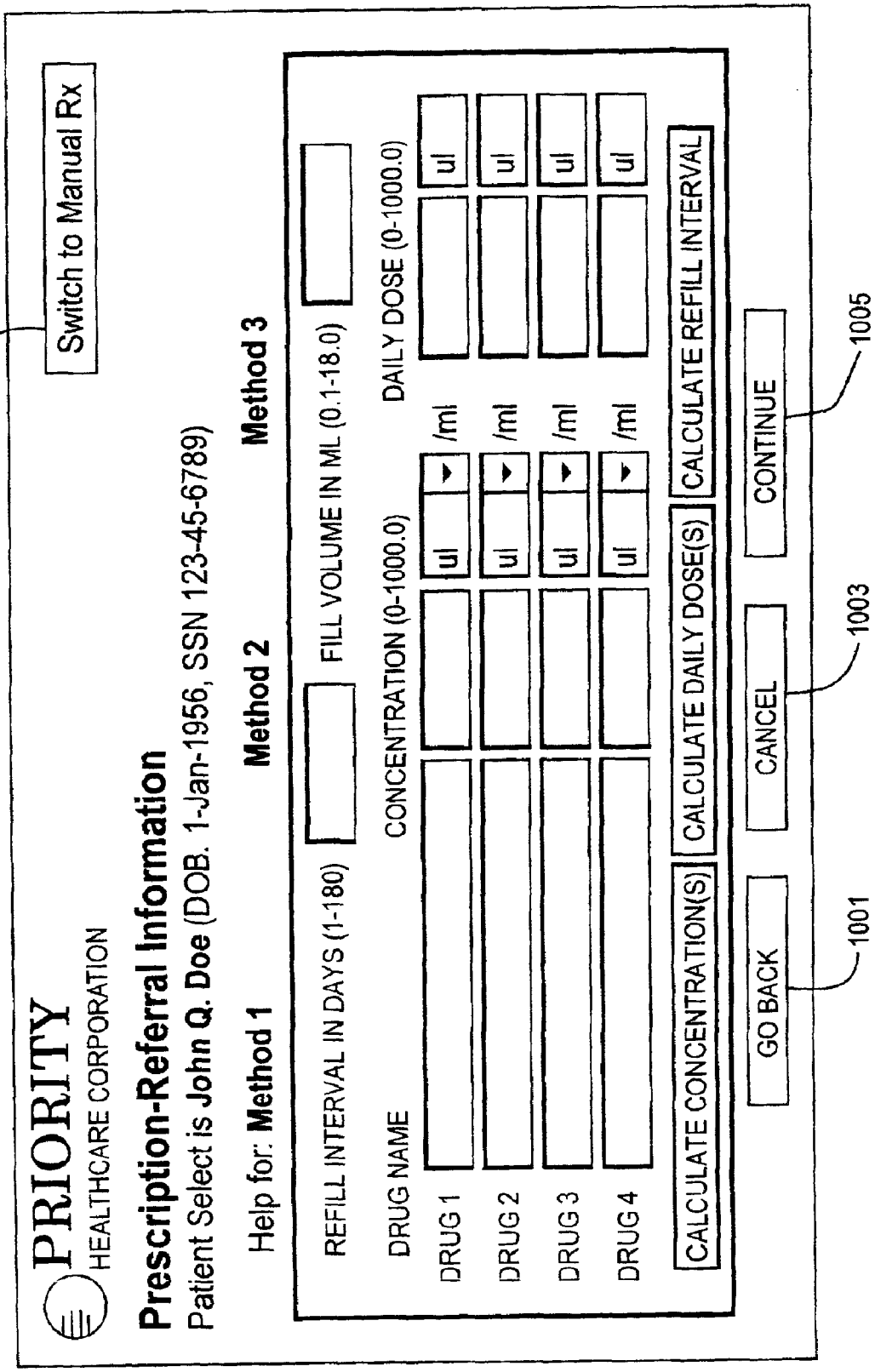
FIG. 12 is a representation of an interface display for a Multiple Drug Calculator function according to one implementation of the present invention.

Moreover, the clinician 12 is able to utilize a "Multiple Drug Calculator" as shown in FIG. 12 and discussed in more detail below with reference to FIGS. 30–32. Instead of using the drug calculator the clinician 12 also has the alternative of manually inputting the prescription information as shown in FIG. 13. By clicking on the "Switch to Manual Rx" GUI element 1202 the clinician 12 is transferred to the Manual Rx function and simply inputs the medications name, concentration, and a daily dosage. From the manual input function the clinician 12 has the option to switch to the calculator shown in FIG. 12 by clicking on the "Switch to Calculator" GUI element 1302. Further, the function can inform the clinician 12 of the implantable device's syringe volume in box 1304 and a delivery or programmed rate in box 1306.

Figure 14:
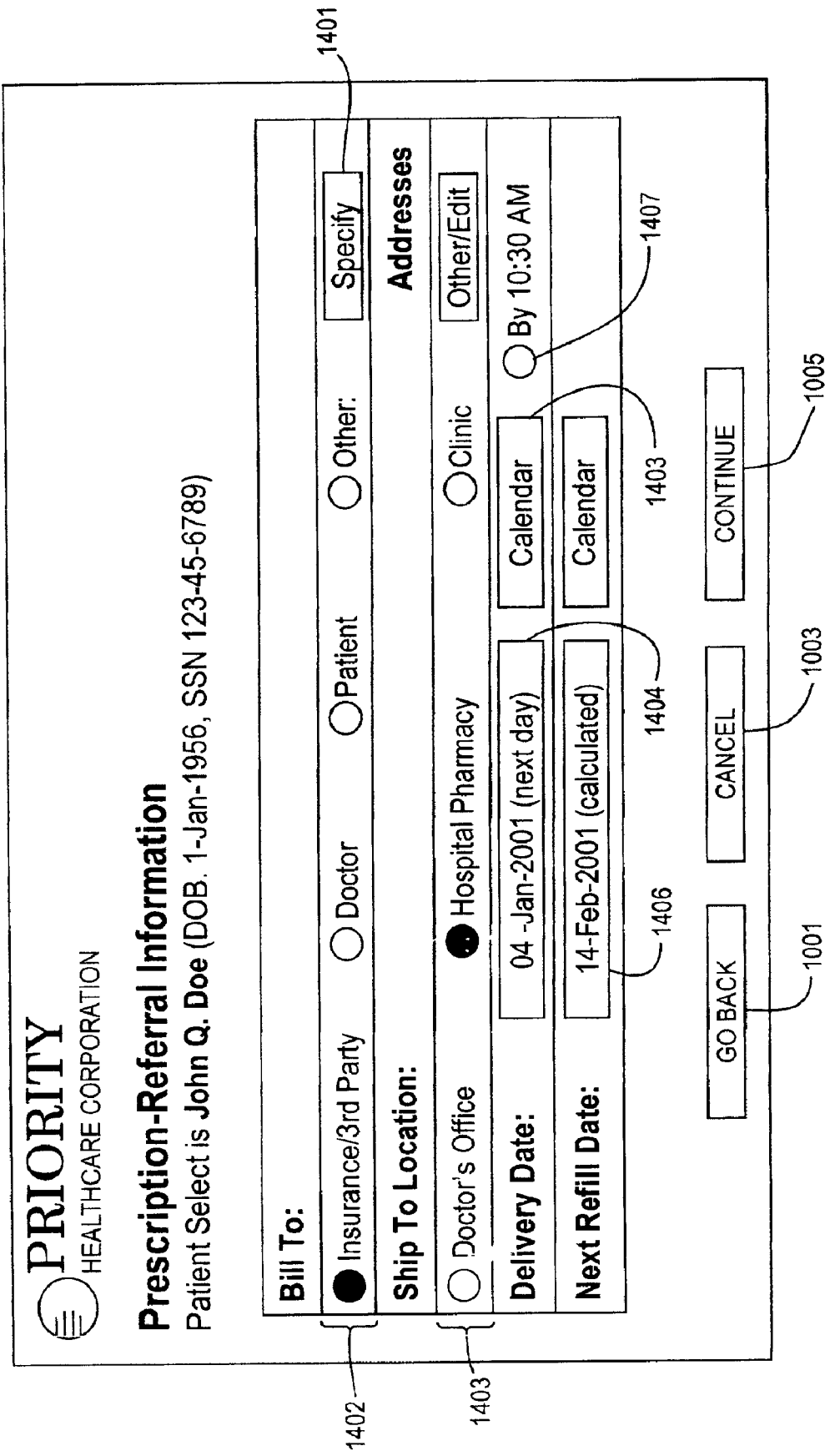
FIG. 14 is a representation of an interface display for a "Set Delivery/Shipping" date function according to one implementation of the present invention.

With reference to FIGS. 14, when the clinician 12 is finished entering a prescription(s) either manually or with the drug calculator, the clinician 12 can set a delivery and shipping date. The clinician 12 can first choose how the prescription will be billed either to an insurance company, a doctor, the patient 10, or to another entity by clicking on one of the status bulbs 1402. The clinician 12 then clicks on the "Specify" GUI element 1401 and a pop-up window can appear where the clinician 12 enters the address of the entity to be billed or chooses from a list of known entities addresses. Next, the clinician 12 chooses a shipping location by choosing one of status bulbs 1403. The clinician 12 can then click on the "Other/Edit" GUI element and go to a pop-up window if an alternate shipping address is desired or if the current selected location's address has changed, then the clinician 12 can enter the necessary changes. The prescription's delivery date is displayed in box 1405 and the next calculated prescription refill date is displayed in box 1406. If either of these dates are incorrect, the clinician 12 can click on the "Calendar" GUI element 1405 to enter a corrected date. The clinician 12 can also specify a time-of-day for the delivery by clicking on status bulb 1407.

Figure 15:
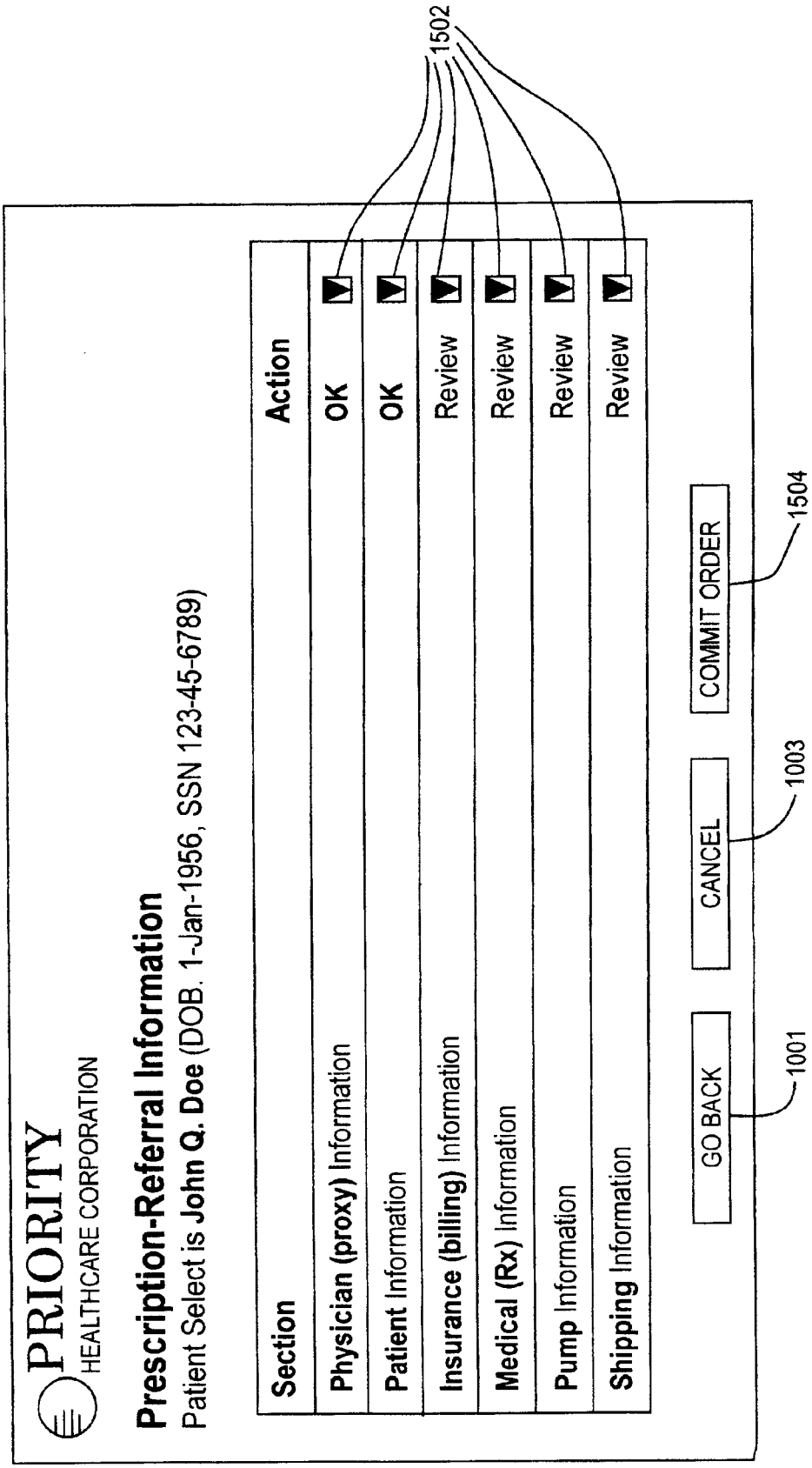
FIG. 15 is a representation of an interface display for an "Order Prescription Confirmation" function according to one implementation of the present invention.

When the clinician 12 is finished and everything is correct, he/she can click on "Continue" GUI element 1005 and go to the Confirmation function as shown in FIG. 15. As shown in FIG. 15 all of the information entered by the clinician 12 is shown for a final review. As the clinician 12 reviews the information he/she is required to click on box 1502 to signify that the clinician 12 has reviewed the information and the information is acceptable. The clinician 12 performing this operation reduces the chances of an error in the prescription. When the clinician 12 is finished reviewing the order, they simply click on the "Commit Order" GUI element 1504 to submit the prescription order to the pharmacy.

Figure 16:
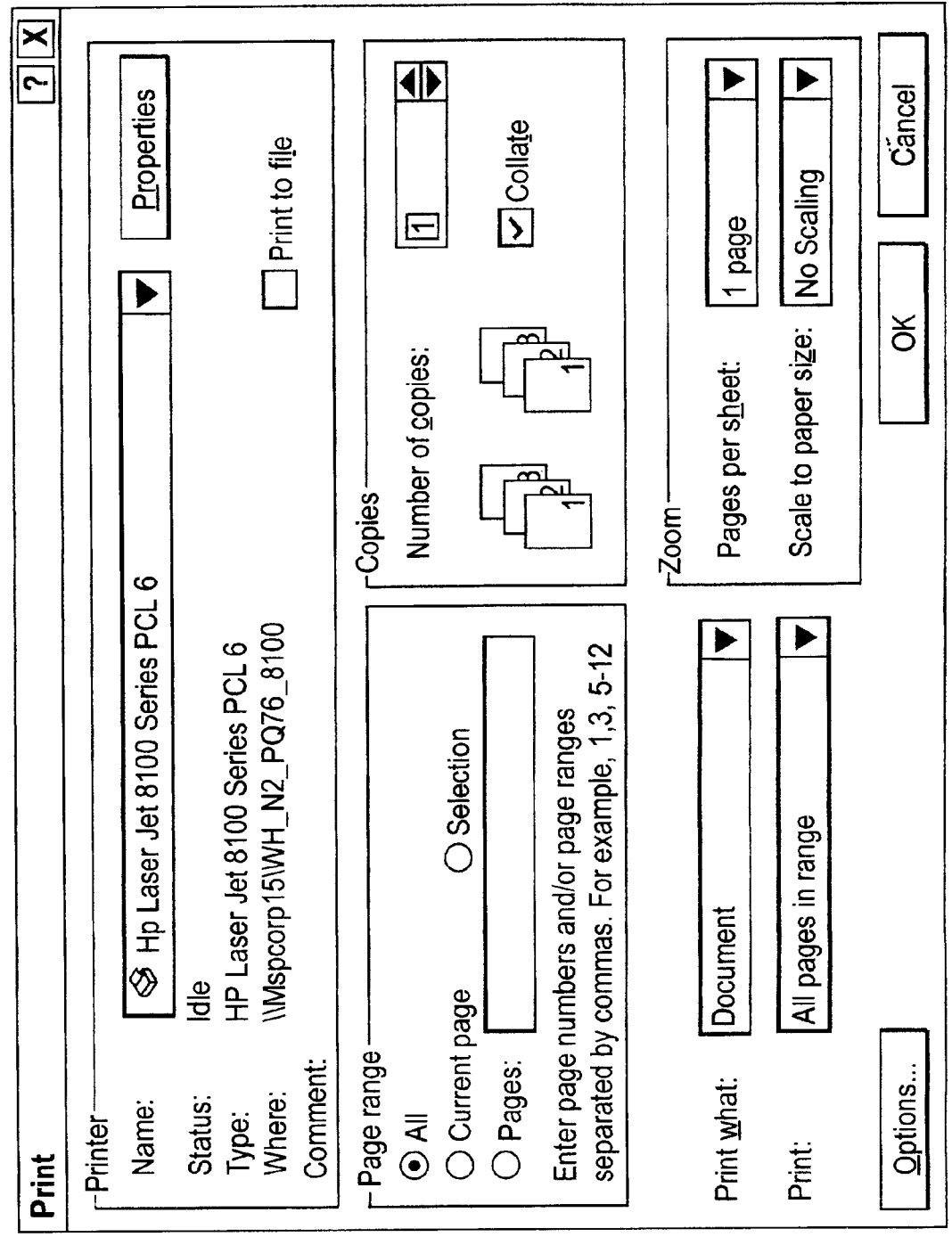
FIG. 16 is a representation of an interface display for a "Fax Order Prescription" form function according to one implementation of the present invention.

Alternatively, the application according to the present invention may generate an Order Prescription Form, or "FAXable form" as shown in FIG. 16, suitable for facsimile communication to a pharmacy. While, in this embodiment, the efficiencies of the central network communication will be reduced, the facsimile form generation will eliminate transcription of the information to an alternate facsimile form; thus eliminating a possible vector for errors. Preferably, the FAXable form is similar to the current Patient Referral Form, but additionally provides for a signature line including the Physician name. The form may also provide the application user name in parenthesis, if different from the physician name. A pharmacy or other agent dispensary will typically require the signature of the physician if the central server does not provide the physician authentication.

Figure 17:
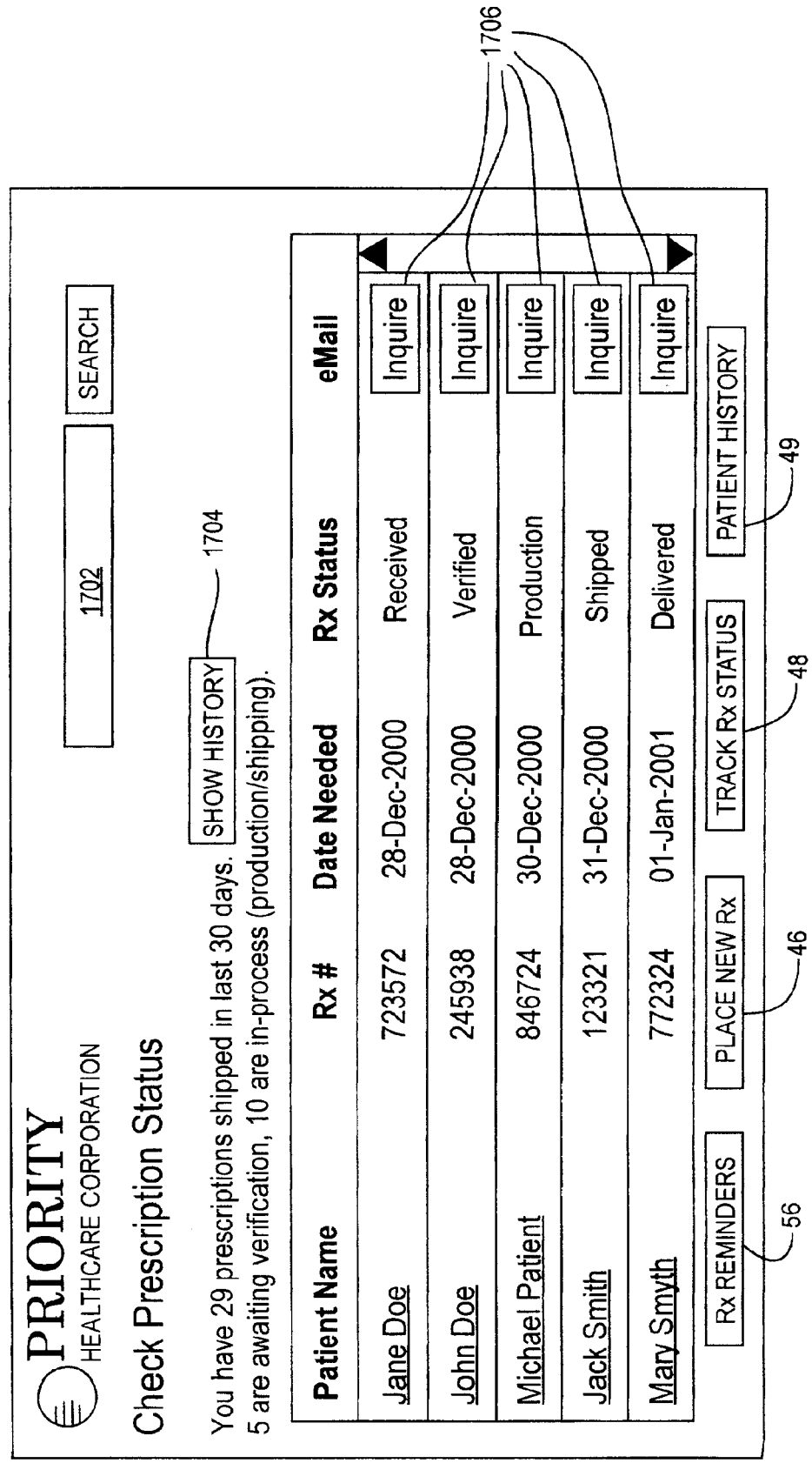
FIG. 17 is a representation of an interface display for a "Tracking Prescription Status" function according to one implementation of the present invention.

The present invention also preferably provides a utility for the tracking of prescription status. This utility is depicted in FIG. 17. The user is able to input a patient 10 name in box 1702 and perform a search for a patient 10 by clicking on the Search GUI element. The user is also able to see a prescription history detailing how many prescriptions have be shipped in a selected time period, how many prescriptions are awaiting verification, or how many prescriptions are in need of production or shipping by clicking on the "Show History" GUI element 1704. As the clinician 12 checks the status of each prescription he/she, if necessary, may inquire into a particular prescription by clicking on "Inquire" GUI element 1706. Preferably, a pop-up window will appear to show the user where the prescription currently is, when it is expected to be delivered, and any other information pertinent to the prescription.

Figure 19:
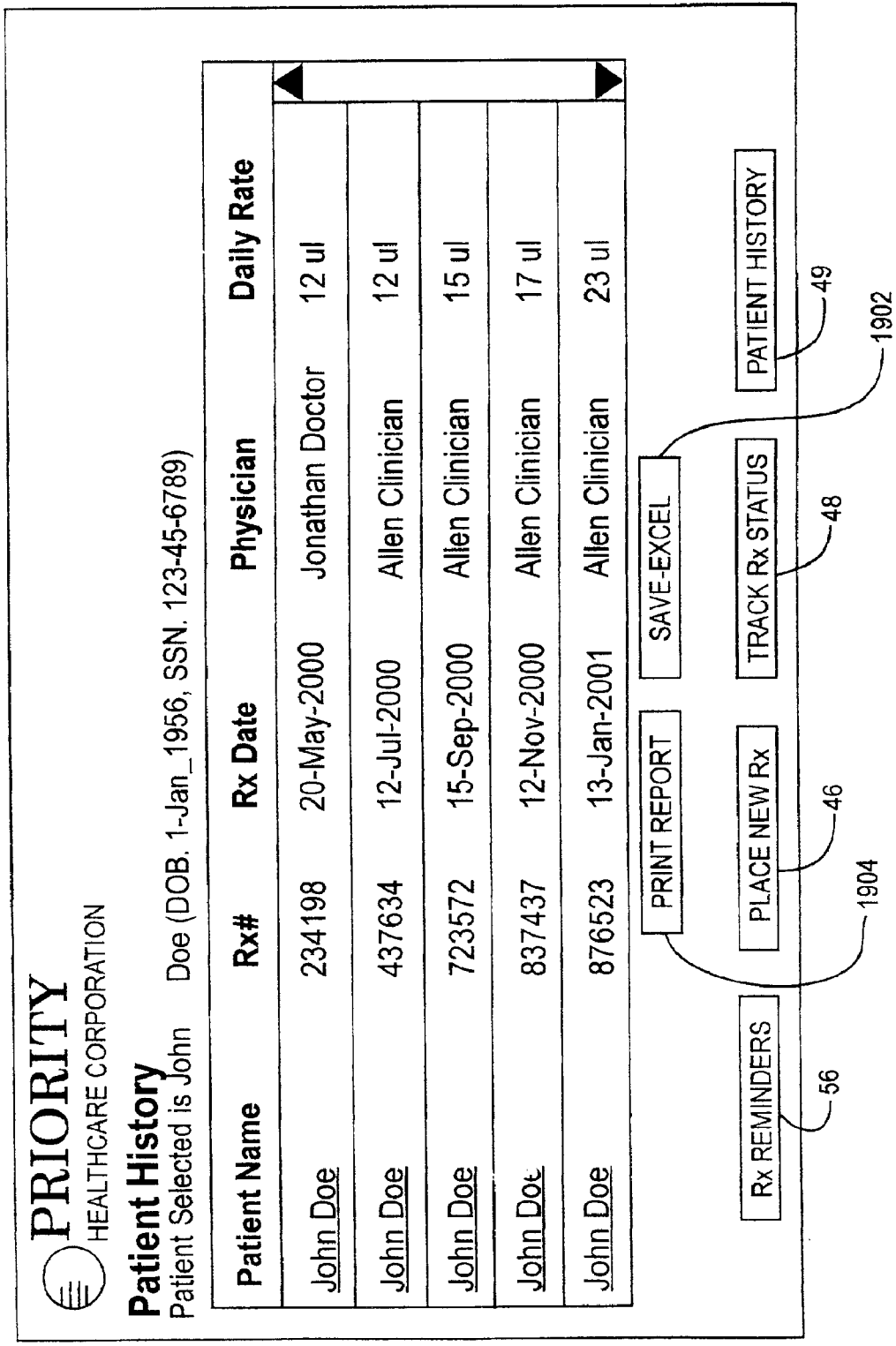
FIG. 19 is another representation of an interface display for a "Patient History" function according to one implementation of the present invention.

It will also be useful to provide the user of the application with a Patient History Report as shown in FIGS. 18 & 19. With reference to FIG. 18, the user is able to input a patient 10 name in box 1802 and perform a search for a patient 10 by clicking on the Search GUI element. The user can also select a patient 10 from a listing of patients. If the clinician 12 desires to see a report on the patient 10, the clinician 12 can click on the "Print Report" GUI element 1804. If the clinician 12 desires to view the patients history individually, he/she can click on the "History/Chart" GUI element 1806 and be linked to the history display function shown in FIG. 19. The user can also check pump info box 1808, which will give all the information related to the patient's implanted device. The patient 10 display function shown in FIG. 19 can display information such as the prescription number, the prescription order date, the authorizing physician, and the daily dosage rate. The clinician 12 then has the option to save the history information into an Excel® file by clicking on "Save-Excel" GUI element 1902 or to print the individualized history by clicking on "Print Report" GUI element 1904.

Figure 20:
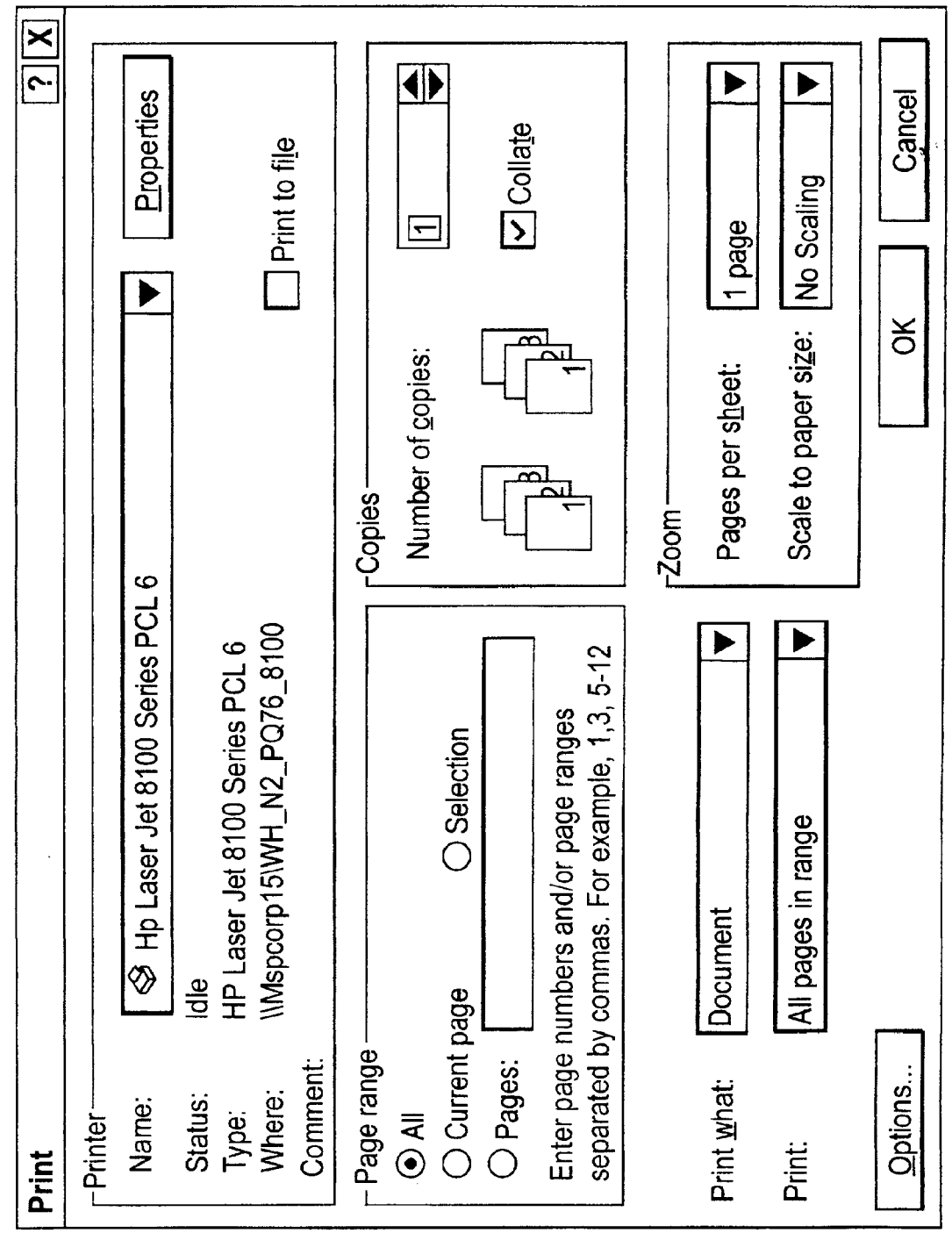
FIG. 20 is a representation of an interface display for a "Patient History Print Report" function according to one implementation of the present invention.

The Patient History Report may be stored locally on the clinician's machine, or may alternatively be formatted to fit a desired paper size, e.g. 8.5"×11", for paper filing as shown in FIG. 20. The central server may also provide storage space, for example, as a courtesy or on a subscription basis, for participating clinicians. In this embodiment, a paper Patient History Report may be dispensed with if desired. In the event that a report is more suitable to "landscape" style printing, the application preferably notifies the user to make a corresponding change in the printer "Properties" menu, if the application according to the present invention is implemented on a "Wintel" style or "Microsoft Windows®" environment. The formatted page may be implemented so as to automatically open the printer dialog to select a printer. There may also be provided under the present invention an Add New Patient, or "Registration Support Function". Under this embodiment, when the "Add New Patient" command is executed from the "Order New Rx" screen, or a "Select Patient" search command does not find the patient 10, the patient 10 registration process will automatically begin. Alternatively, the user, for the patient-not-found scenario, may specify the launching of this process. In these cases the "Order Prescription" process will preferably immediately follow completion of new patient 10 registration. Executing the "Rx" command, e.g., via "Rx" GUI element button may begin the "Order Prescription" process for the corresponding patient 10 listed.

Figure 21:
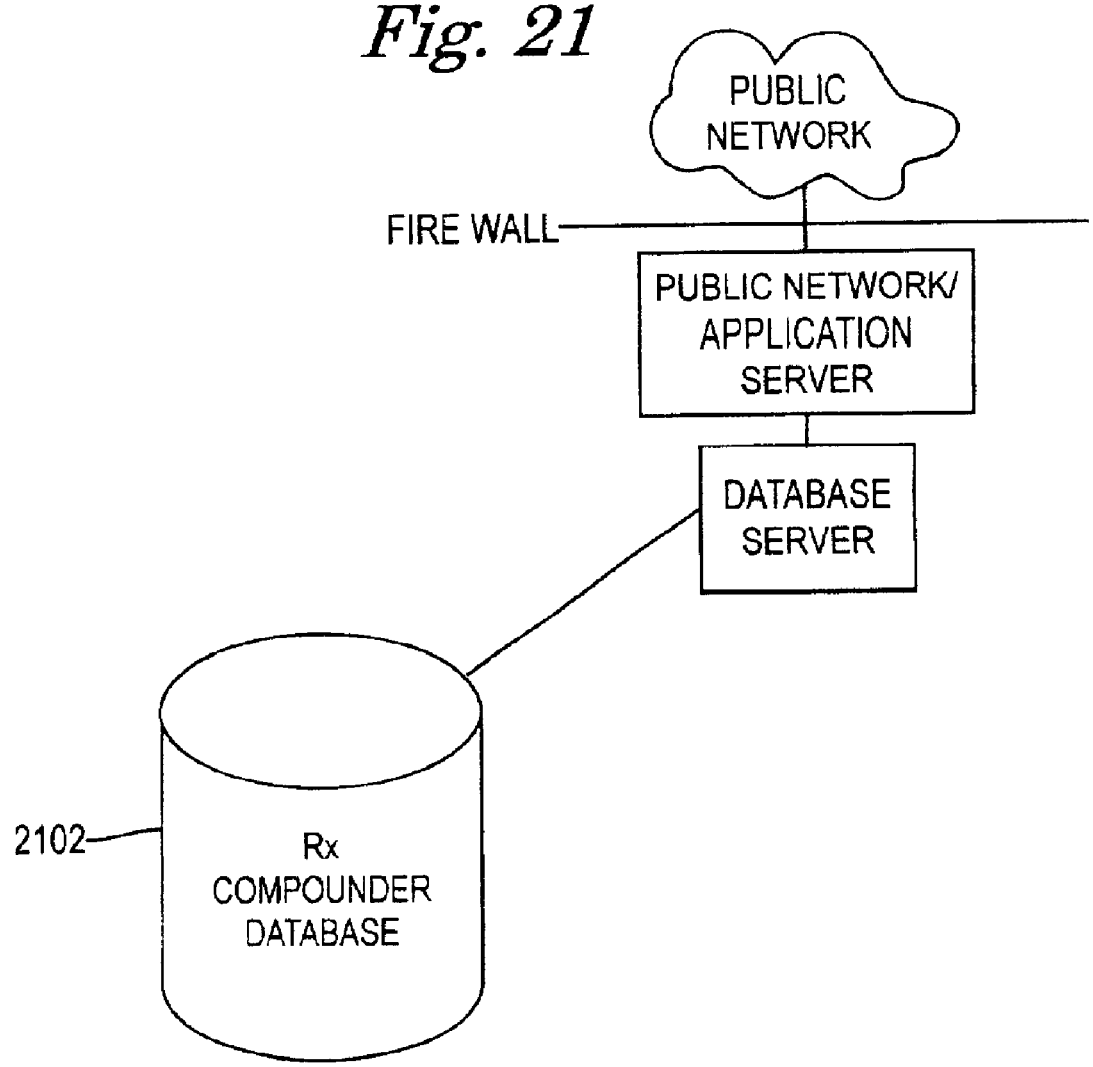
FIG. 21 is a network architecture diagram of a database server.
Figure 23:
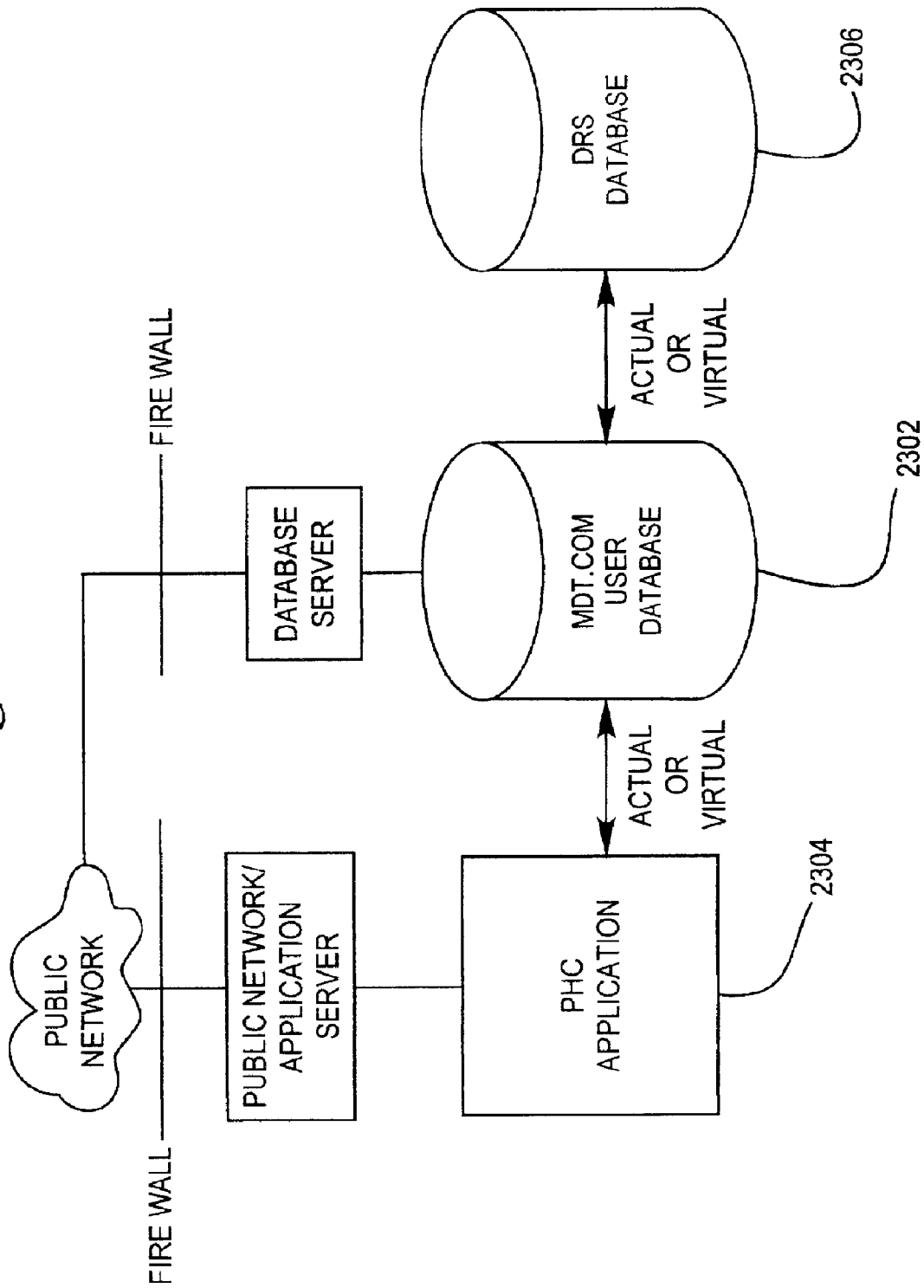
FIG. 23 is a network architecture diagram of a database server.

With reference to FIGS. 21, to avoid duplicate patient 10 registration entries, preferably the "Add New Patient" function will check existing database 2102 for duplicates and prompt the user if this is the same person or a different patient 10 with the same name. This check for existing patients will in particular be preferable when the "Add New Patient" routine was manually launched, as opposed to being launched automatically by the application in the patient-not-found scenario.

Upon adding a new patient 10 according to the process above, a "Patient Registration" process (see FIG. 22) or similar routine may be executed. Here a user would be prompted to enter information about the patient 10 including: name, address, phone number, and social security number. A system according to the present invention may also provide a utility by which a clinician 12 may lookup a patient 10 in a central server database (see FIG. 23). The MDT.COM user database 2302 would first be searched for any patients already matching the inputted patient 10. Then the application would check the pharmacist's database 2304 as well as the clinician's database 2306. If the patient 10 is found in any of the databases, information boxes in the patient 10 registration function (FIG. 22), including Patient emergency contact and medical information (FIG. 24), Patient Insurance information (FIG. 25), and Patient Medical Device information are backfilled in to reduce the amount of user input. However, if the patient 10 is not identified in any database, the user must then input all of the information in FIGS. 22, and 24–26 manually. Ideally, however, under this utility, the "Patient Search" command may be executed from the "Patient Registration" screen (see FIGS. 24–26) and the backfilling process can be used for these screens as well. In this case the "Update" process will immediately follow the search. In order to avoid duplicate patient 10 registration entries, the "Patient Search" function preferably will check the existing database(s) for duplicates and prompt the user to indicate whether this is the same person or a different patient 10 with the same name.

FIG. 26 also displays a representation of the drug pump registration page utilized by the clinician 12. This page as discussed above, is where the clinician 12 can input the drug pump's serial number and other associated data and then obtains extensive data surrounding the drug pump.

Figure 27:
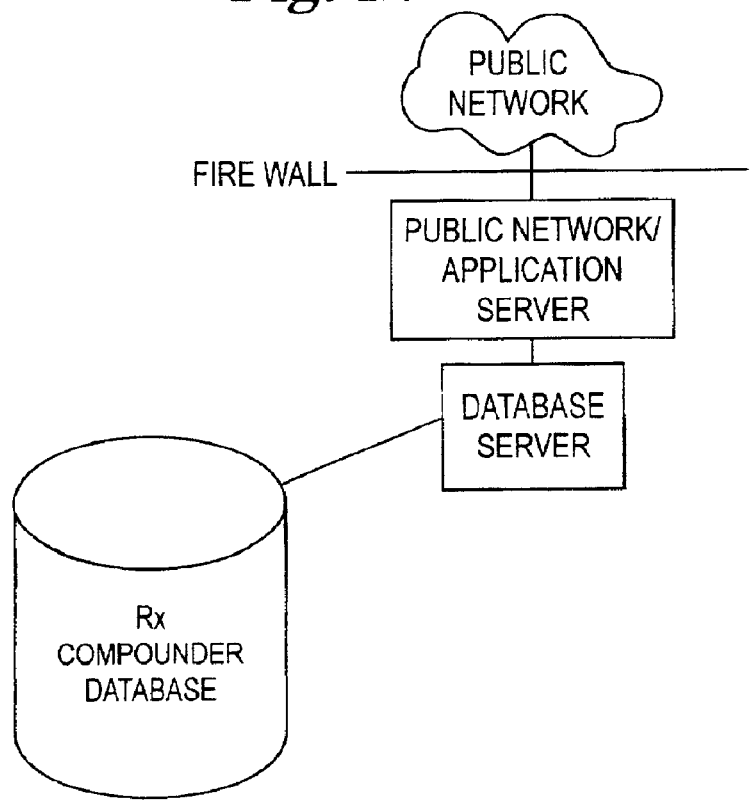
FIG. 27 is a network architecture diagram of a database server.
Figure 28:
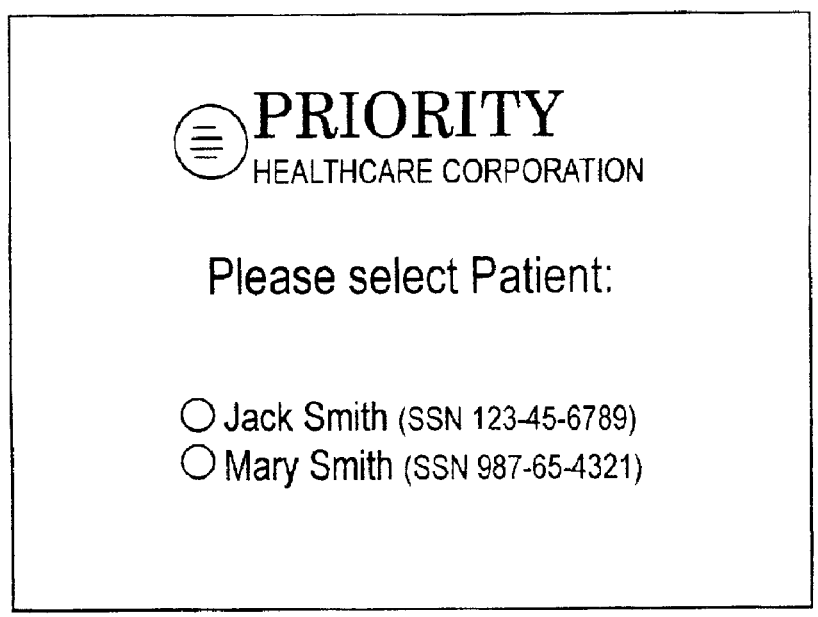
FIG. 28 is a representation of an interface display for a "Select Patient" function according to one implementation of the present invention.

With reference to FIG. 27, in a preferred embodiment, an alternate Select Patient (Search) Support Function is provided in addition to that described above. In this function, the "Select Patient" search command queries database 27 using name and/or social security number (or other suitable unique record identifier) to resolve a unique record. If the search function does not find the patient 10, the patient 10 registration process will begin. The screen following the "Select Patient" function is dependent upon the invoking command. As with the embodiments of the present invention described above, a routine is provided to resolve patients with similar names. In this embodiment, for example, a "pop-up selection box" may appear and list each patient 10 with sufficient detail to enable the clinician 12 to select the desired patient 10, preferably while minimizing the disclosure of individually-identifiable patient 10 data for persons who are not patients of the user or the user's clinical entity. A radio button array may be provided for indication of the selected patient 10 as shown in FIG. 28. As described above, if the patient 10 is not found, the "Patient Registration" process may be launched, preferably automatically.

The present invention provides a computerized or otherwise automated system that may be used by a medical clinician 12 to assist the clinician 12 in managing patients receiving various drug infusion therapies by means of implanted medical devices. This system may be referred to generally as a "Dosage Calculator," although many functions are presented in a preferred embodiment that provide functionality beyond simple calculation of dosage for a particular desired treatment outcome in a particular patient 10. By way of example, the present invention will be specifically described as it may be implemented to aid in the administration and management of therapy by means of implanted drug pumps that may carry out intrathecal, vascular, subcutaneous, or other systemic or local therapeutic agent, such as an injectable drug. The instant invention is anticipated to prove compatible with the Medtronic® SynchroMed® implantable drug infusion system, for example. By entering known information concerning the desired therapeutic agent, such as one or more drugs intended for intrathecal use, the present invention will provide information necessary to prepare the solution or agent, and correctly program the implantable device to administer the therapy.

With reference to FIG. 29, the present invention can be expected to provide benefits in implantable drug pump administration and operation. In a preferred embodiment, a computer application implementing the present invention such as a Java® Applet, can be used to perform the following calculations if the applicable variables are available or supplied to the application: With more discussion below, the system may be used to calculate the concentration of drug(s) in the pump given refill interval, reservoir size, concentration units and daily dose. The system can calculate the daily dose of the drug given refill interval, reservoir size, drug concentration units and concentration of drug(s) in the pump. Finally, the system will preferably be able to calculate the refill interval for the pump given drug concentration units, concentration of drug(s) in the pump, and daily dose. In addition to these calculations, the system will preferably enable a clinician 12 to conduct a variety of alternative speculative or planning scenarios in varying the above variables and viewing the corresponding outcome that may be expected. Because of the improved information and planning available via use of the instant invention, the invention may be expected to reduce the risk that an implanted pump in use runs dry. This outcome is, naturally, to be avoided, because of the risk of causing abrupt drug withdrawal reactions in the implant patient. In addition to this benefit, however, the present invention minimizes the potential for overdose, and also accommodates deletions or additions to the drug mixture or solution. This drug mixture or solution may be, for example, an intrathecal application drug mixture.

The system may also implement a "patient record recall" utility or function. For example, a clinician 12 may be given the capability to access a record of a therapeutic agent solution or mixture, and modify a most recently administered solution. In addition, the invention preferably provides the ability to view patient 10 drug history and assess drug and dosage trends that are being experienced by the patient 10.

The present invention, used in conjunction for example with a remotely located server interface, provides opportunities for a clinician 12 to take steps to confirm the safety or desired effect of a contemplated therapy regimen. Accordingly, in addition to the basic features described above, an implementation of the present invention preferably provides a mechanism for measuring the frequency of use of calculator features. This may be implemented in conjunction with the Therapy Support Services provided by copending application Ser. No. 60/278,821, filed Mar. 26, 2001, assigned to a common assignee as the instant invention, and filed on a date even herewith, the disclosure of which is hereby incorporated by reference into this application in its entirety. In addition, the interface presented to an end user preferably contains hyperlinks to information files, web pages, or other server or network resources, containing stability reference on selected drug(s) and concentration(s) that are being contemplated by a physician.

Figure 30:
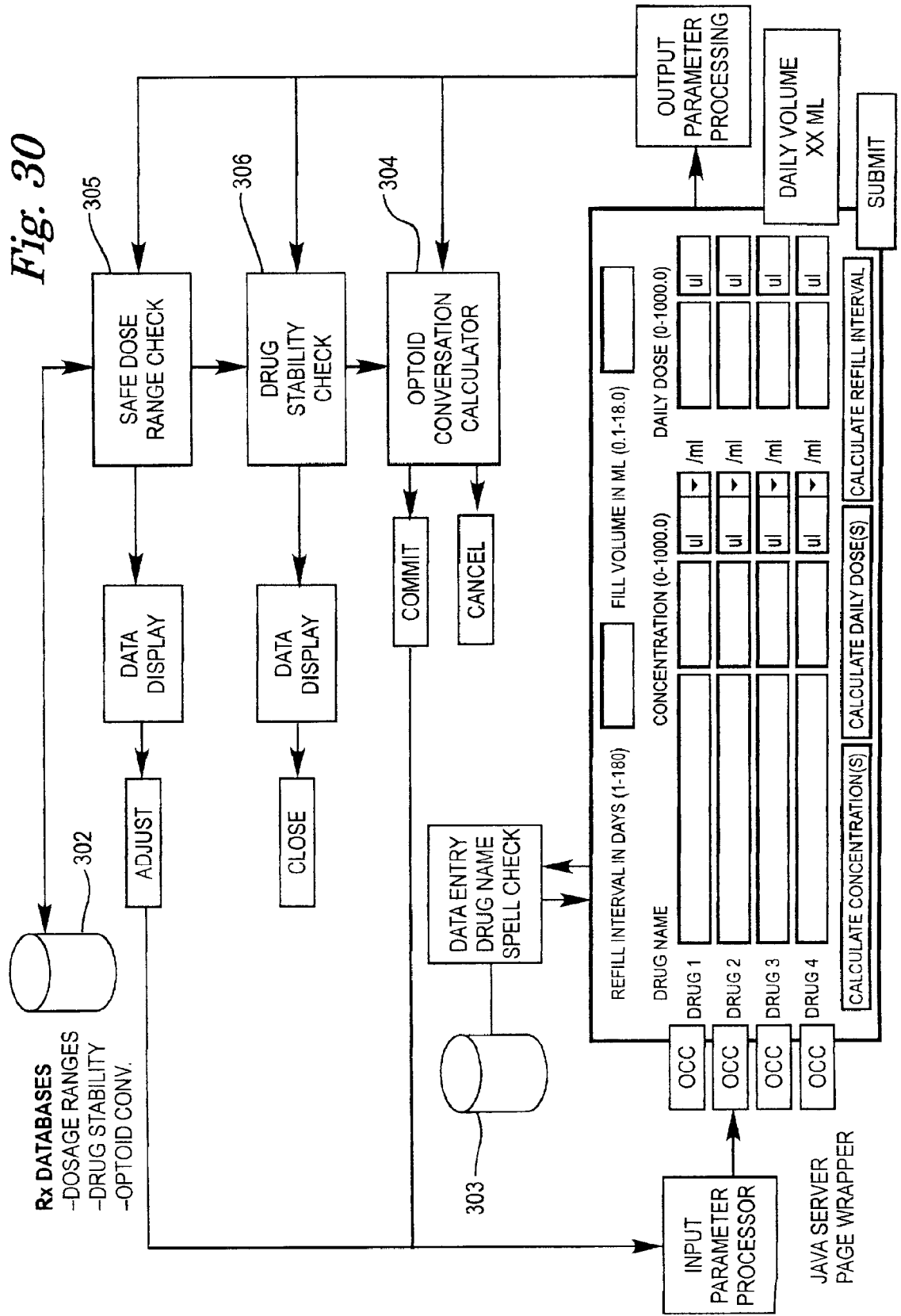
FIG. 30 is a representation of an interface display according to one implementation of a multiple function drug calculator and flow chart of operation for the drug calculator.

With reference to FIG. 30, a representation of a multiple function drug calculator interface is shown in addition to a flow diagram representing the drug calculator's functionality. As stated above, the technical advantage of the drug calculator is the support the clinician 12 receives during the prescription process and the optimization the capabilities of the implantable drug pump and the therapeutic substances. Further, the calculator provides improved safety and therapy efficacy as will be discussed in detail below.

In a preferred embodiment the calculator is an interactive Internet Web based application. The calculator program has input and output parameters which coordinate data exchange between the calculator and the Java Server Pages (JSP) and the Web structure. In a preferred embodiment, the calculator is implemented using java applets, which can handle in excess of 4 drug combinations. Initially, the clinician 12 must enter the desired therapeutic agent's name, concentration, and a daily dosage. When the clinician 12 has finished inputting this information, they simply click on a GUI element button to enter this information into database 303. After processing the drugs and possible combinations, the program outputs information to the clinician 12 such as a daily infusion volume, which is the sum of the drug dosages, and a refill interval, which is the period of time when the drug pump reservoir must be refilled with therapeutic agents.

Figure 31:
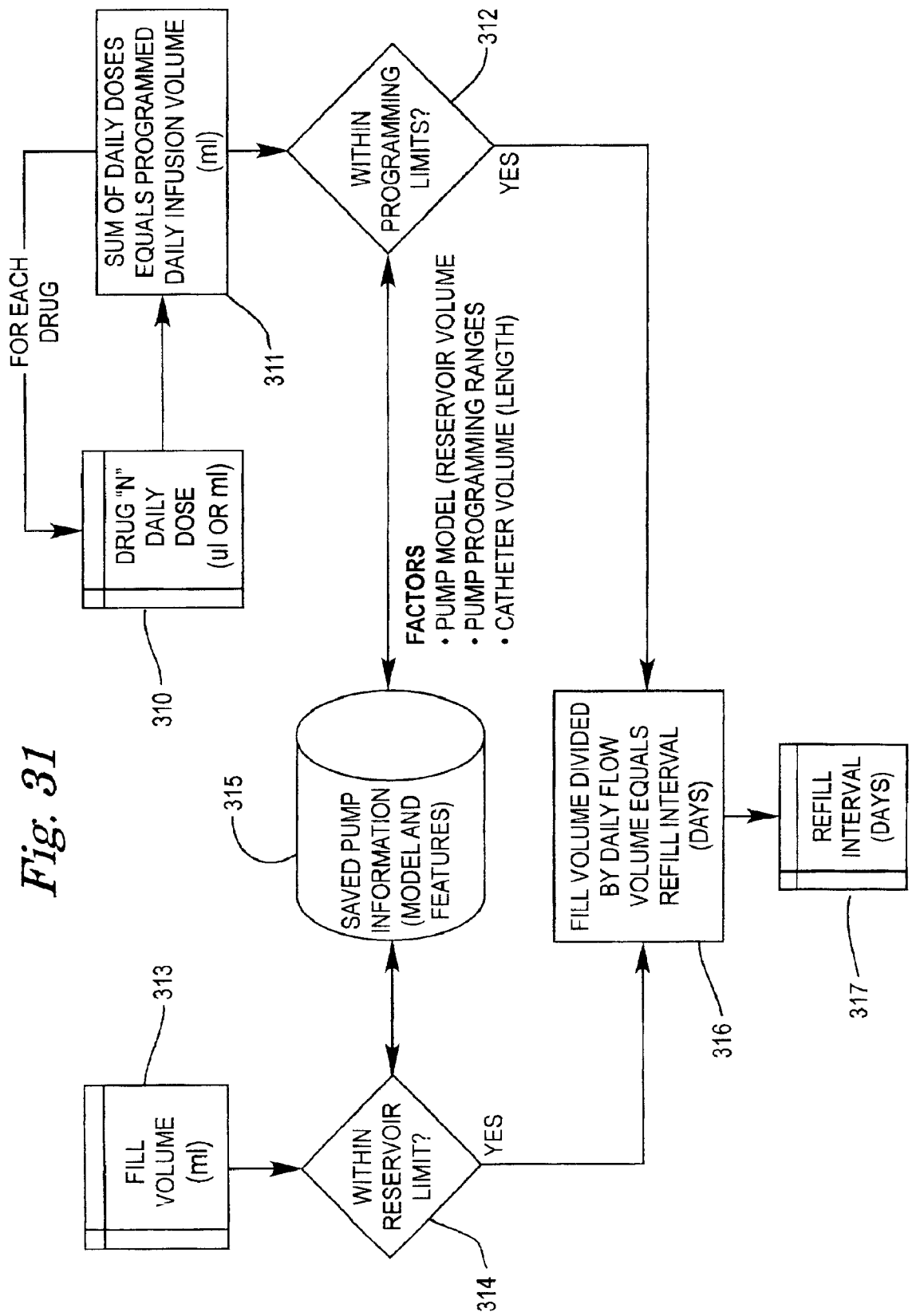
FIG. 31 is a flow diagram representation of the refill interval calculation according to one implementation of a multiple function drug calculator.

With reference to FIGS. 30 & 31, a flow diagram of the refill interval calculation is shown. As the clinician 12 inputs the therapeutic agents and their dosages 310), the calculator program sums the daily doses of the therapeutic agents 311 to determine the daily infusion volume. The calculator program then determines whether the daily infusion volume is within programming limits 312. The programming limits are stored in a database and are comprised of factors including but not limited to: the pump model installed, the pump's programming ranges, and the catheter volume (length). If the daily infusion volume is not within programming limits, the clinician 12 if forced to alter his/her original therapeutic agent prescription.

The clinician 12 is required to input a drug fill volume box, which is the total volume of therapeutic agents prescribed (313). The calculator then determines whether this volume is within the pump's reservoir limits 314. The reservoir limit is determined from preprogrammed pump information 315 located in the database, which includes information such as the pump's model and features. If the fill volume is greater than the reservoir limit, then the clinician 12 is forced to alter his/her original drug prescription. However, if the daily infusion volume is within the pump reservoir's respective limits, then the calculator program divides the fill volume by the daily flow volume 316 and the result is the refill interval in days 317. The refill interval calculation thus insures that the patient 10 is not submitted to unnecessary surgery to refill a drug pump, which could have been postponed several more months.

The present invention is also well suited to provide an Opioid Conversion Calculator (OCC) 304 for dosages of opioids and related therapeutic agents. The OCC program allows a user to input the current therapeutic substance(s) name, concentration, and dosage in their respective input boxes and then perform a database lookup of equivalent therapeutic substances, dosages, and ranges. The drug conversions are performed utilizing industry standard algorithms. The OCC program allows clinicians the option to modify or change a therapeutic substance to a new optoid when needed or necessary due to a allergies, drug interactions, or drug shortages. Once the clinician 12 has viewed his options to modify or change a therapeutic substance, they can then either cancel the conversion or commit the conversion into the input parameters. Canceling the conversion simply returns the clinician 12 back to the drug calculator interface where the clinician 12. If the clinician 12 commits the conversion, the new therapeutic substances are then entered into the drug calculator interface and will be utilized throughout the rest of the prescription process.

Figure 32:
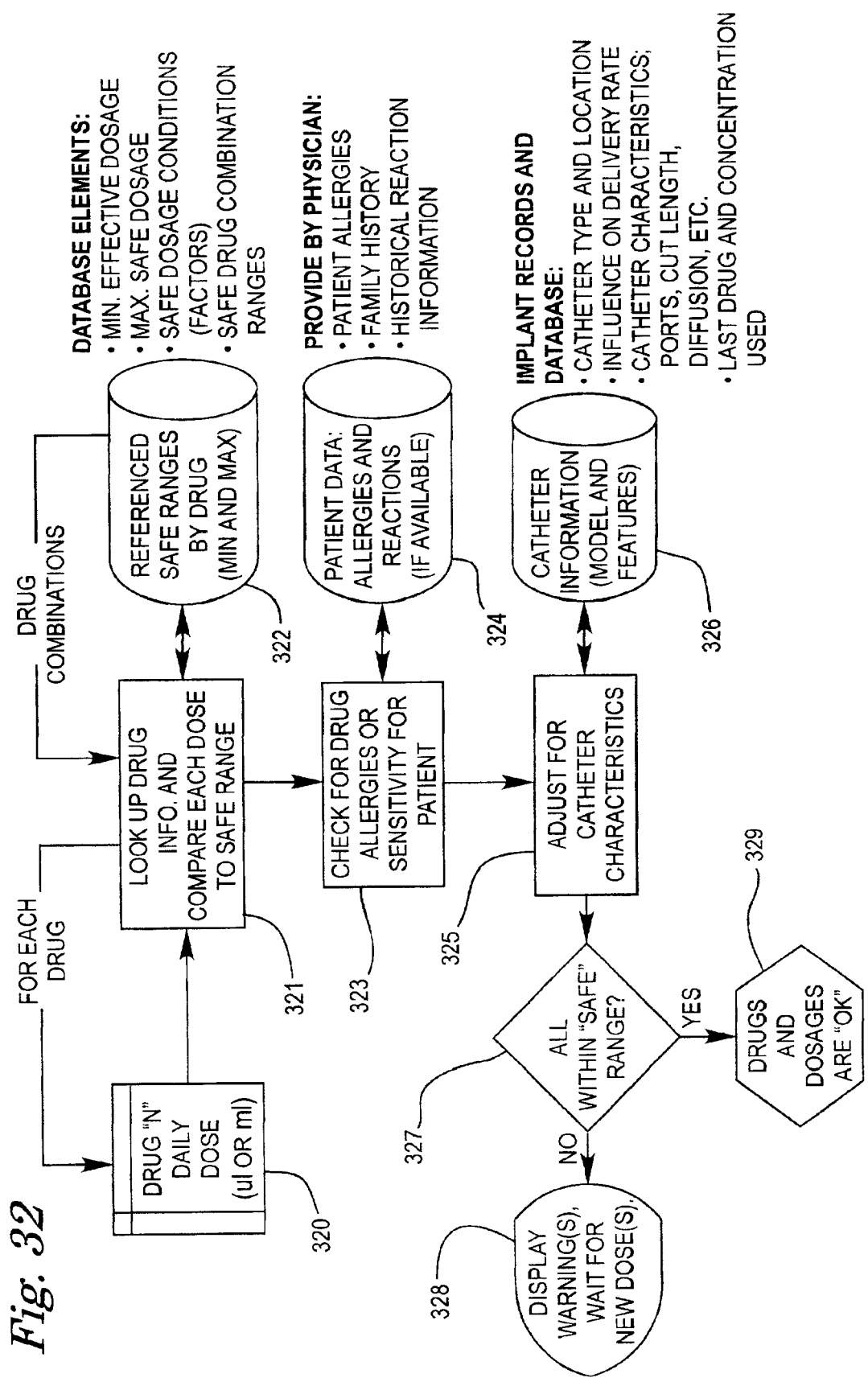
FIG. 32 is a flow diagram representation of the safe dosage range check operation according to one implementation of a multiple function drug calculator.

With reference to FIGS. 30 & 32, a flow diagram for a safe dosage range check operation is shown 305 FIG. 30. As therapeutic substances are inputted into the calculator 320, the program performs a therapeutic substance information lookup and determines whether each therapeutic substance requested and its dosage prescribed is within a safe prescribable range 321. The calculator obtains safe prescribable range information from drug database 302 (FIG. 30) 322, FIG. 32. Database 302 contains information including, but not limited to, the minimum effective dosage of the therapeutic substance, the maximum safe dosage of the therapeutic substance, safe dosage conditions, and safe therapeutic substance combination ranges. It is of note that the safety check program compares the prescribed dose of each therapeutic substance to "normal" prescribing industry standards (i.e., $+/-3\sigma$). In addition, the program checks for drug allergies or drug sensitivities the patient 10 may have 323. The safe dosage program obtains the drug allergy and reaction information from the physician's database 324, containing information such as the patient's allergies, family history, drug reaction historical information, and patient 10 body weight, height, and therapy information. The safe dosage program then determines whether any adjustments are necessary due to any catheter characteristics 325. Catheter information is gathered from the pump's implant records and from database 302 (FIG. 30) 326 including, but not limited to, such information as the type of catheter used and its location in the patient 10, any influence the catheter may have on the therapeutic substance delivery rate, the catheter's ports, cut length, and diffusion rate, and the last therapeutic substance and its concentration used with the catheter. Finally, the safe check program determines, from the three comparisons made above, if the therapeutic substances prescribed are within a safe prescribable range 327. If the drugs prescribed are outside of the safe range, a warning is displayed until a new dosage is submitted by the clinician 12 328. However, if the drug prescription is within the safe range then the prescription is displayed to the clinician 12 and submitted to the calculator program 329. Thus the clinician 12 is insured that the patient 10 will not be harmed by erroneous prescriptions.

Figure 33:
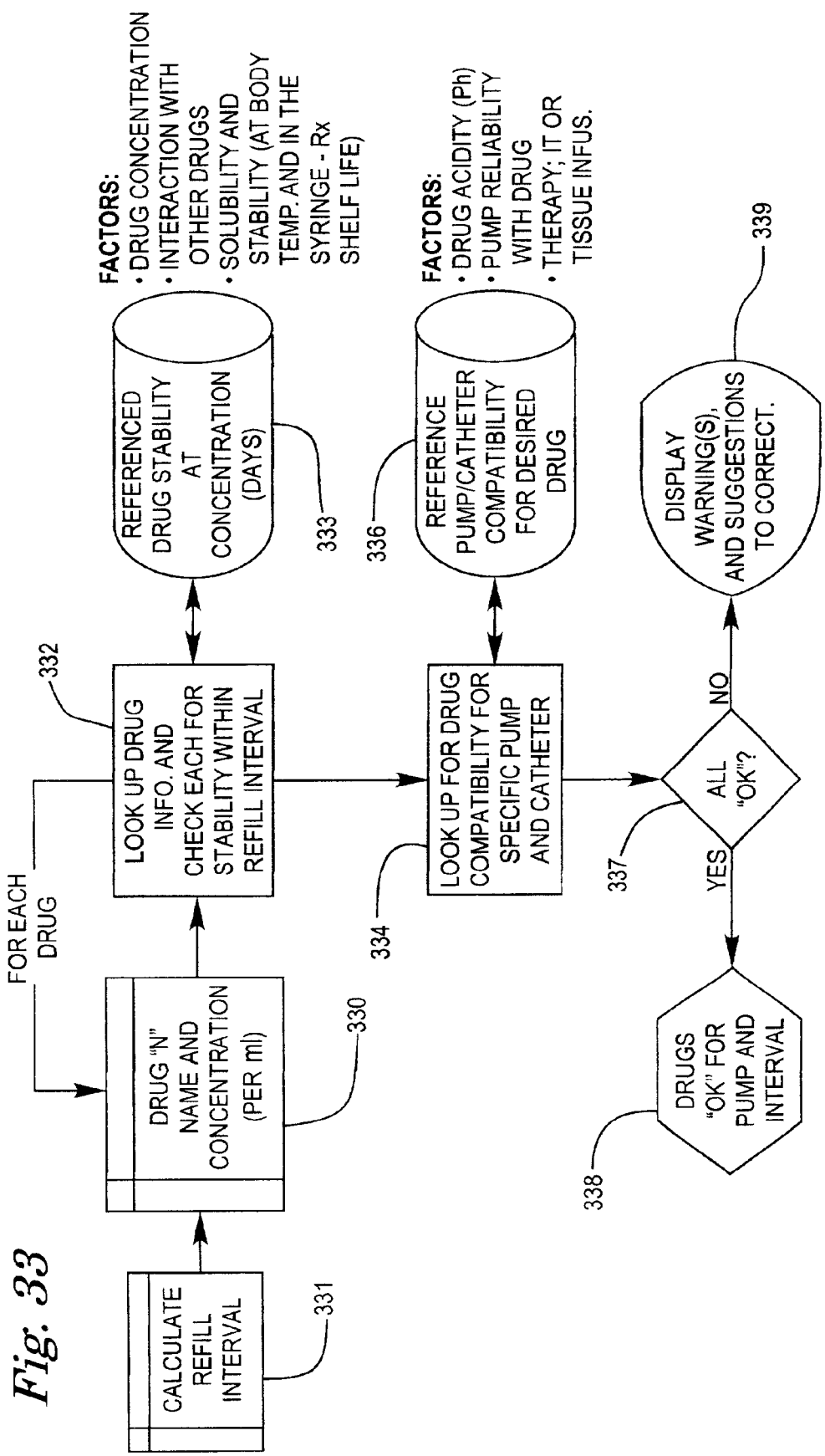
FIG. 33 is a flow diagram representation of the drug stability/compatibility checking operation according to one implementation of a multiple function drug calculator.

With reference to FIGS. 30 & 33, a flow diagram representation for a drug stability/compatibility checking function is shown box 306 of FIG. 30. Upon the clinician 12 entering the therapeutic substance's name and concentration 330, FIG. 33, the calculator program will calculate a refill interval 331 as described above. The stability program then takes the therapeutic substance's names, refill interval, concentration data and verifies that each therapeutic substance will be stable within the refill interval 332. The program utilizes database 302 containing stability and concentration information including, but not limited to, the therapeutic substance's concentration, the therapeutic substance's interaction with other therapeutic substances, the therapeutic substance's solubility and stability at body temperature, and the therapeutic substance's syringe shelf life 333. The stability check program then performs a lookup in database 302 for the therapeutic substance's compatibility with specific pumps and catheters 334. This information is referenced from database 302, which contains information, including but not limited to, the drug pump/catheter compatibility for a desired therapeutic substance 335, the therapeutic substance's acidity, and the pump's reliability with the therapeutic substance, and any therapy, IT, or tissue infuse 336. Next the drug stability program determines if the stability checks performed above have been completed successfully 337. If both checks were performed and no problems with stability or compatibility were encountered, then the therapeutic substances are deemed proper for the pump and the pump interval 338. However, if the compatibility or stability checks were unsuccessful, then the calculator displays a warning, a suggestion for correction, and then waits until a correction is made 339. Thus the clinician 12 is insured of no harmful interaction or reaction of therapeutic substances.

Another safety check function, which may be desired by a clinician 12, is a drug name "spell check" feature. In this way, a clinician 12 may enter a drug name according to the spelling that they believe accurate. If the therapeutic agent entered does not exist, but is similar in spelling to several actual therapeutic agents, the user may be presented with a selection menu of actual agents. The user may also be presented with such a list in the event that the entered therapeutic agent does exist, but is nonetheless quite similar in spelling to alternative therapeutic agents that may have been intended.

The present invention may be implemented in any number of GUI element environments and platforms suitable for use over a data network. For example, the present invention may be suitably implemented as one or more Java® Applets (i.e., Java® byte-code executable code sections which may be transmitted over a network and run in a html browser environment) to accept input variables from a central or clinic database. The Applets may also accept suitable input variables to build a suitable GUI element display at the client location, as is known in the art. These input variables may include base font, font color and size, background color, and display size (relative/ratio or pixel H×W). Output of a central server application implementing the present invention is preferably made to hidden JSP/web variables for processing form input, in a manner that will be transparent to the end user.

It will be preferable to allow an end user to execute a "Print" icon or command, so that a hard copy record may be generated for the patient's file or chart in facilities where paper files are maintained.

It will be appreciated that the present invention can take many forms and embodiments. It is not intended that the embodiment of the invention presented herein should limit the scope thereof.

What is claimed is:

1. A data communications server system for managing intrathecal therapy, comprising:

a computerized network of patient nodes, clinician nodes, pharmaceutical nodes, drug pump manufacturer nodes; and means for configuring implantable drug pumps with data gathered from a patient, a clinician, a drug pump manufacturer, therapeutic agent producer, and a pharmacy.

2. The data communication server system of claim 1, wherein the implanted drug pump collects at least a portion of the data.

3. The data communications server system of claim 1, wherein the intrathecal therapy distributed comprises instructions to implanted drug pumps to optimize the life of the drug pump and the intrathecal therapy.

4. A computerized method of collecting and utilizing distributed patient, clinician, implantable drug pump manufacturer, therapeutic agent producer, and pharmacy data, comprising the steps of:

a. providing a data communications network from which each remote node may access, directly or indirectly, a central server system;

b. providing to the remote network nodes a computerized interface to resources of the server;

c. gathering via the remote network node computerized interfaces individual patient implantable drug pump data from the drug pump manufacturer;

d. aggregating the patient, clinician, drug pump manufacturer, therapeutic agent producer, and pharmacy data; and e. distributing the patient, clinician, drug pump manufacturer, therapeutic agent producer, and pharmacy data to remote network nodes administered by clinicians.

5. The computerized method of claim 4, wherein the central server system comprises a network of servers.

6. The computerized method of claim 4, wherein the computerized interface to the central server system is implemented as an html browser utility.

7. The computerized method of claim 4, wherein the resources of the central server system comprise a body of empirical data regarding implantable drug pumps.

8. The computerized method of claim 7, wherein the resources of the central server system further comprise a system of comparing and analyzing the body of empirical data.

9. The computerized method of claim 7, wherein the empirical data regarding implanted drug pumps comprises data identifiable to individual drug pumps.

10. The computerized method of claim 9, wherein the data identifiable to individual drug pumps may be accessed by the patient, the clinician, the pharmacy, and the drug pump manufacturer to which this data pertains.

11. The computerized method of claim 10, wherein the data identifiable to individual drug pumps is protected by an encryption protocol when accessed.

12. The computerized method of claim 11, wherein the security protocol protecting the data identifiable to individual drug pumps is a secure socket layer.

13. The computerized method of claim 11, wherein the security protocol protecting the data identifiable to individual drug pumps is the https protocol.

14. The computerized method of claim 11, wherein a user attempting to access data identifiable to an individual drug pump must authenticate themselves prior to receiving the data.

15. The computerized method of claim 14, wherein the authentication to which a user is subject comprises strong authentication.

16. A real-time information management system for implantable drug pumps, comprising:

a computerized data communication server network that allows patients, clinicians, pharmacists, and drug pump manufactures to view, analyze and display data concerning the implantable drug pump;

a server-based interface to disseminate to patients, clinicians, pharmacists, and drug pump manufactures information about their drug pumps;

means configuring implantable drug pumps to manage intrathecal therapy based upon patient, clinician, drug pump manufacturer, therapeutic agent producer, and pharmacy information.

17. The real-time information management system of claim 16, wherein the information about implantable drug pumps comprises technology developments, clinical trials, and medication utilized by the drug pump.

18. A computerized method of communicating in real time between patients, clinicians, pharmacists, and implanted drug pump manufactures comprising the steps of:
   a. capturing implanted drug pump device data;
   b. storing the implanted drug pump device data on a central server system;
   c. analyzing and distributing aggregate drug pump device data;
   d. displaying drug pump-specific data in real time over a public network; and
   e. dispensing intrathecal therapy based upon patient, clinician, drug pump manufacturer, therapeutic agent producer, and pharmacy information.

19. The computerized method of claim 18 wherein the patient is able to monitor intrathecal therapy.

20. The method of claim 18 wherein the displaying of drug pump specific data over a public network is done using a secure protocol with an authenticated client.

21. A data communications server system for managing intrathecal therapy, comprising:
   a computerized network comprising patient nodes, clinician nodes, drug pump manufacturer nodes, and pharmacy nodes;
   means for prescribing therapeutic substances with data gathered from at least one patient, at least one clinician, at least one drug pump manufacturer, at least one therapeutic agent producer, and at least one pharmacy;
   means for configuring implantable drug pumps with data gathered from at least one patient, at least one clinician, at least one drug pump manufacturer, at least one therapeutic agent producer, and at least one pharmacy.

22. The data communication server system of claim 21, wherein the means for prescribing therapeutic substance includes a therapeutic substance refill interval.

23. The data communications server system of claim 21, wherein the means for prescribing therapeutic substance includes a therapeutic substance stability safeguard.

24. The data communications server system of claim 21, wherein the means for prescribing therapeutic substance includes a therapeutic substance compatibility safeguard.

25. The data communications server system of claim 21, wherein the means for prescribing therapeutic substance includes an optoid conversion means.

26. The data communications server system of claim 21, wherein the means for prescribing therapeutic substance includes a therapeutic substance safe dosage range safeguard.

27. A computerized method of communicating in real time between patients, clinicians, pharmacists, and implanted drug pump manufactures, comprising the steps of:
   a. capturing implanted drug pump device data;
   b. storing the implanted drug pump device data on a central server system;
   c. analyzing and distributing aggregate drug pump device data;
   d. displaying drug pump-specific data in real time over a public network;
   e. prescribing therapeutic substances; and
   f. dispensing intrathecal therapy based upon patient, clinician, drug pump manufacturer, therapeutic agent producer, and pharmacy information.

28. The method of claim 27 wherein the prescribing of therapeutic substances includes calculating a refill interval optimized to prevent unnecessary surgeries.

29. The method of claim 27 wherein the prescribing of therapeutic substances includes calculating a safe dosage to prevent prescribing erroneous dosages.

30. The method of claim 27 wherein the prescribing of therapeutic substances includes calculating the substance's stability and compatibility with the drug pump to prevent harmful interaction.

31. The method of claim 27 wherein the prescribing of therapeutic substances includes an optoid conversion calculator.

* * * * *